United States Patent
Kuhn

(10) Patent No.: US 8,521,245 B2
(45) Date of Patent: Aug. 27, 2013

(54) METHOD AND APPARATUS FOR POST-SHOCK EVALUATION USING TISSUE OXYGENATION MEASUREMENTS

(75) Inventor: Jonathan L. Kuhn, Ham Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 834 days.

(21) Appl. No.: 12/609,538

(22) Filed: Oct. 30, 2009

(65) Prior Publication Data
US 2011/0066018 A1 Mar. 17, 2011

Related U.S. Application Data

(60) Provisional application No. 61/241,505, filed on Sep. 11, 2009.

(51) Int. Cl.
*A61B 5/00* (2006.01)

(52) U.S. Cl.
USPC .................................................. 600/323

(58) Field of Classification Search
USPC .................................................. 600/323
See application file for complete search history.

(56) References Cited

U.S. PATENT DOCUMENTS

| | | | |
|---|---|---|---|
| 4,180,078 A | 12/1979 | Anderson | |
| 4,202,339 A | 5/1980 | Wirtzfeld et al. | |
| 4,230,122 A | 10/1980 | Lubbers et al. | |
| 4,399,820 A | 8/1983 | Wirtzfeld et al. | |
| 4,467,807 A | 8/1984 | Bornzin | |
| 4,548,209 A | 10/1985 | Wielders et al. | |
| 4,567,892 A | 2/1986 | Plicchi et al. | |
| 4,750,495 A | 6/1988 | Moore et al. | |
| 4,967,748 A | 11/1990 | Cohen | |
| 5,007,423 A | 4/1991 | Branstetter et al. | |
| 5,163,427 A | 11/1992 | Keimel | |
| 5,176,137 A | 1/1993 | Erickson et al. | |
| 5,188,105 A | 2/1993 | Keimel | |
| 5,188,108 A | 2/1993 | Secker | |
| 5,193,535 A | 3/1993 | Bardy et al. | |

(Continued)

FOREIGN PATENT DOCUMENTS

| | | |
|---|---|---|
| EP | 760476 | 3/1997 |
| EP | 1764034 | 3/2007 |

(Continued)

OTHER PUBLICATIONS

Myers, Dean E., Noninvasive Method for Measuring Local Hemoglobin Oxygen Saturation in Tissue Using Wide Gap Second Derivative Near-Infrared Spectroscopy, Journal of Biomedical Optics 10(3), 034017 (May/Jun. 2005).

(Continued)

*Primary Examiner* — Rodney Fuller
(74) *Attorney, Agent, or Firm* — Michael C. Soldner

(57) ABSTRACT

A method and apparatus for controlling delivery of therapy that includes an emitting portion emitting light at a predetermined emitted light intensity to a volume of tissue at a plurality of wavelengths, and a detecting portion detecting the emitted light scattered by the volume of tissue to generate corresponding detected light intensity output signals. A control module adjusts the detected light intensity output signals for shifts in intensity corresponding to the emitted light intensity, and determines a tissue oxygenation index in response to only the adjusted detected light intensity output signals, and a therapy delivery module controlling therapy in response to the determined tissue oxygenation index.

22 Claims, 10 Drawing Sheets

(56) References Cited

U.S. PATENT DOCUMENTS

| | | |
|---|---|---|
| 5,213,098 A | 5/1993 | Bennett |
| 5,218,962 A | 6/1993 | Mannheimer et al. |
| 5,227,181 A | 7/1993 | Knudsen |
| 5,354,316 A | 10/1994 | Keimel |
| 5,364,316 A | 11/1994 | Brambilla |
| 5,385,143 A | 1/1995 | Aoyagi |
| 5,398,680 A | 3/1995 | Polson et al. |
| 5,431,172 A | 7/1995 | Hoegnelid et al. |
| 5,464,434 A | 11/1995 | Alt |
| 5,470,345 A | 11/1995 | Hassler et al. |
| 5,531,714 A | 7/1996 | Dahn et al. |
| 5,545,186 A | 8/1996 | Olson et al. |
| 5,588,427 A | 12/1996 | Tien |
| 5,593,431 A | 1/1997 | Sheldon |
| 5,596,986 A | 1/1997 | Goldfarb |
| 5,683,432 A | 11/1997 | Goedeke et al. |
| 5,725,219 A | 3/1998 | Gilbert |
| 5,752,519 A | 5/1998 | Benaron et al. |
| 5,769,785 A | 6/1998 | Diab et al. |
| 5,855,593 A | 1/1999 | Olson et al. |
| 5,879,294 A | 3/1999 | Anderson et al. |
| 5,902,326 A | 5/1999 | Lessar et al. |
| 6,144,866 A | 11/2000 | Miesel et al. |
| 6,198,952 B1 | 3/2001 | Miesel |
| 6,226,540 B1 | 5/2001 | Bernreuter |
| 6,236,882 B1 | 5/2001 | Lee et al. |
| 6,292,698 B1 | 9/2001 | Duffin et al. |
| 6,377,840 B1 | 4/2002 | Gritsenko et al. |
| 6,473,632 B1 | 10/2002 | Myers |
| 6,481,899 B2 | 11/2002 | Quast et al. |
| 6,487,343 B1 | 11/2002 | Lewandowski et al. |
| 6,512,940 B1 | 1/2003 | Brabec et al. |
| 6,522,915 B1 | 2/2003 | Ceballos et al. |
| 6,587,703 B2 | 7/2003 | Cheng et al. |
| 6,599,250 B2 | 7/2003 | Webb et al. |
| 6,615,064 B1 | 9/2003 | Aldrich |
| 6,622,046 B2 | 9/2003 | Fraley et al. |
| 6,667,803 B1 | 12/2003 | Flessland et al. |
| 6,682,135 B2 | 1/2004 | Zheng |
| 6,738,667 B2 | 5/2004 | Deno et al. |
| 6,839,583 B1 | 1/2005 | Lewandowski et al. |
| 6,839,592 B2 | 1/2005 | Grandjean |
| 6,850,787 B2 | 2/2005 | Weber et al. |
| 6,892,006 B2 | 5/2005 | Lewandowski et al. |
| 6,944,488 B2 | 9/2005 | Roberts |
| 6,997,879 B1 | 2/2006 | Turcott |
| 7,043,294 B1 | 5/2006 | Paris |
| 7,096,064 B2 | 8/2006 | Deno et al. |
| 7,127,278 B2 | 10/2006 | Melker et al. |
| 7,164,948 B2 | 1/2007 | Struble et al. |
| 7,165,893 B2 | 1/2007 | Schmitz |
| 7,177,686 B1 | 2/2007 | Turcott |
| 7,239,385 B2 | 7/2007 | Schmitz et al. |
| 7,239,901 B2 | 7/2007 | Gritsenko |
| 7,277,757 B2 | 10/2007 | Casavant et al. |
| 7,302,294 B2 | 11/2007 | Kamath et al. |
| 7,809,441 B2 * | 10/2010 | Kane et al. .................. 607/22 |
| 7,991,448 B2 | 8/2011 | Edgar, Jr. et al. |
| 8,038,626 B2 * | 10/2011 | Cinbis et al. .................. 600/508 |
| 8,055,321 B2 * | 11/2011 | Bernreuter .................. 600/323 |
| 8,090,432 B2 * | 1/2012 | Cinbis et al. .................. 600/473 |
| 8,165,662 B2 * | 4/2012 | Cinbis et al. .................. 600/473 |
| 2003/0004412 A1 | 1/2003 | Izatt et al. |
| 2003/0065365 A1 | 4/2003 | Zhu et al. |
| 2003/0144584 A1 | 7/2003 | Mendelson |
| 2003/0187480 A1 | 10/2003 | KenKnight et al. |
| 2003/0199956 A1 | 10/2003 | Struble et al. |
| 2004/0024297 A1 | 2/2004 | Chen et al. |
| 2004/0220629 A1 | 11/2004 | Kamath et al. |
| 2005/0119586 A1 | 6/2005 | Coyle et al. |
| 2005/0148832 A1 | 7/2005 | Reghabi et al. |
| 2005/0277818 A1 | 12/2005 | Myers |
| 2006/0009685 A1 | 1/2006 | Finarov et al. |
| 2006/0025827 A1 | 2/2006 | Hatlesad et al. |
| 2006/0106293 A1 | 5/2006 | Fantini |
| 2006/0253007 A1 | 11/2006 | Cheng et al. |
| 2007/0203406 A1 | 8/2007 | Anderson et al. |
| 2007/0239052 A1 | 10/2007 | Bhunia |
| 2007/0239053 A1 | 10/2007 | Bhunia |
| 2007/0239215 A1 | 10/2007 | Bhunia et al. |
| 2007/0255148 A1 | 11/2007 | Bhunia |
| 2008/0004513 A1 | 1/2008 | Walker et al. |
| 2008/0015424 A1 | 1/2008 | Bernreuter |
| 2008/0103538 A1 | 5/2008 | Walker et al. |
| 2008/0208011 A1 | 8/2008 | Shuler |
| 2008/0208020 A1 | 8/2008 | Cinbis et al. |
| 2008/0208269 A1 | 8/2008 | Cinbis et al. |
| 2008/0306390 A1 | 12/2008 | Cinbis |
| 2010/0130840 A1 | 5/2010 | Isaacson |
| 2010/0185252 A1 | 7/2010 | Bjorling et al. |
| 2010/0292548 A1 | 11/2010 | Baker, Jr. et al. |
| 2010/0292549 A1 | 11/2010 | Shuler |
| 2010/0317943 A1 | 12/2010 | Kuhn et al. |
| 2011/0066017 A1 * | 3/2011 | Kuhn .................. 600/333 |

FOREIGN PATENT DOCUMENTS

| | | |
|---|---|---|
| EP | 19555653 | 8/2008 |
| GB | 1419701 | 12/1975 |
| WO | 9825669 | 6/1998 |
| WO | 03077750 | 9/2003 |
| WO | 2004091719 | 10/2004 |
| WO | 2007012931 | 2/2007 |
| WO | 2008105698 | 9/2008 |
| WO | 2008118042 | 10/2008 |
| WO | 2008151263 | 12/2008 |

OTHER PUBLICATIONS

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305, Jul. 29, 2003.

St Jude Medical, ME 317: Design for Manufacturability, Implantable Pulse Generator Optical Sensing System, Jun. 1, 2004, 225 pages.

M.N. Ericson et al., Development of an Implantable Oximetry-Based Organ Perfusion Sensor, Proceeding of the 26th Annual International Conference of the IEEE EMBS, Sep. 1-5, 2004, pp. 2235-2238.

Jr Wilson et al., Noninvasive Detection of Skeletal Muscle Underperfusion with Near-Infrared Spectroscopy ion Patients with Heart Failure; Circulation: Journal of the American Heart Association, 1989;80; pp. 1668-1674.

Benaron, David A., Quantitative Clinical Non-Pulsatile and Localized Visible Light Oximter: Design of the T-Stat (Trade Market) Tissue Oximeter, Stanford University School of Medicine, Palo Alto, CA USA 94305, Jul. 30, 2003.

* cited by examiner

METHOD AND APPARATUS FOR POST-SHOCK EVALUATION USING TISSUE OXYGENATION MEASUREMENTS

RELATED APPLICATION

The present disclosure claims priority and other benefits from U.S. Provisional Patent Application Ser. No. 61/241,505, filed Sep. 11, 2009, entitled "METHOD OF POST-SHOCK EVALUATION USING TISSUE OXYGENATION MEASUREMENTS", incorporated herein by reference in it's entirety.

CROSS-REFERENCE TO RELATED APPLICATION

Cross-reference is hereby made to the commonly-assigned related U.S. application Ser. No. 12/609,514, entitled "METHOD AND APPARATUS FOR POST-SHOCK EVALUATION USING TISSUE OXYGENATION MEASUREMENTS", to Kuhn, filed concurrently herewith and incorporated herein by reference in it's entirety.

TECHNICAL FIELD

The disclosure relates generally to medical devices and, in particular, to an implantable medical device and associated method for detecting success or failure of a delivered shock therapy in treating an arrhythmia.

BACKGROUND

Cardiac arrhythmias can be detected and treated by implantable cardioverter defibrillators (ICDs). ICDs typically monitor an intracardiac electrogram (EGM) signal to determine a patient's heart rhythm. When tachycardia or fibrillation are detected, electrical stimulation therapies are delivered, which may include pacing therapies and/or cardioversion/defibrillation shock therapies. Occasionally, a shock therapy is not successful in converting the arrhythmia back to normal sinus rhythm. In this case, another shock therapy is typically delivered as soon as possible. In order to determine success of a shock therapy, the ICD must detect the presence of the normal sinus rhythm. However, the EGM signal can be disrupted due to the shock delivery and other factors can delay detection of the heart rhythm and may result in unnecessarily repeating a shock therapy. The delivery of a shock therapy can be painful to the patient and uses considerable battery charge. As such, it is desirable to avoid continuing deliver of shock therapy when, for example, a preceding shock has been successful. Methods for evaluating the heart's response to a shock therapy that is not exclusively dependent on the EGM signal is needed.

DETAILED DESCRIPTION

Figure 1:
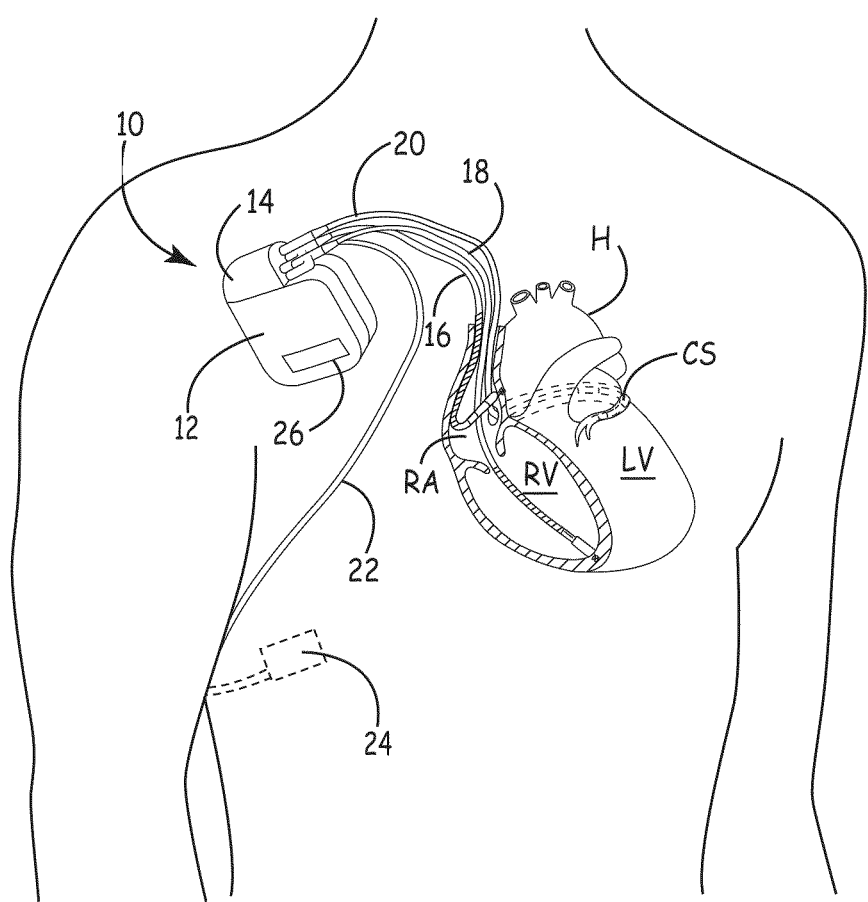
FIG. 1 is a schematic drawing of an implantable medical device (IMD) configured for both monitoring the function of and delivering therapy to a patient's heart.

In the following description, references are made to illustrative embodiments. It is understood that other embodiments may be utilized without departing from the scope of the disclosure. In some instances, for purposes of clarity, the same reference numbers may be used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

In various embodiments described herein, an optical sensor is used to monitor tissue oxygenation in a measurement tissue volume. The measurement volume is the volume of tissue (including blood) in the optical path of the sensor. The term "tissue oxygenation" as used herein refers to the availability of oxygen to a localized tissue volume and thus refers generally to the availability of oxygenated hemoglobin.

The term "total hemoglobin volume fraction" (HbT) refers to the concentration of red blood cells in a measurement volume carrying hemoglobin and thus relates to the total hemoglobin concentration as a fraction of a measurement volume. Stated differently, the total hemoglobin volume fraction, which can be expressed as a percentage, is the volume percentage of red blood cells carrying oxygenated and deoxygenated hemoglobin in the measurement volume. Thus a measurement of HbT will include contributions from red blood cells present in any arteries, capillaries, and veins which may be present in the measurement volume.

Generally speaking, when the availability of oxygen to a body tissue is being monitored, the optical sensor is positioned such that the measurement volume extends through a relatively uniform tissue volume such that optical sensor signals used to compute measurements of tissue oxygenation correlate to the absolute tissue oxygen saturation ($O_2$Sat) and HbT in the microcirculation of the measurement volume.

Absolute tissue oxygen saturation is the portion (or percentage) of the total hemoglobin that is in an oxygenated state. More specifically, $O_2$Sat relates to the available hemoglobin binding sites holding an oxygen molecule. Thus, "tissue oxygenation monitoring" as used herein refers to monitoring both $O_2$Sat (or an index thereof) and HbT (or an index thereof). Tissue oxygenation monitoring may involve determining absolute measurements of $O_2$Sat and HbT, determining trends of these measurements, determining indices of oxygenation measurements or trends of indices. When either $O_2$Sat or HbT or measurements correlated thereto are reduced, a blood-perfused tissue can become hypoxic.

Reduced perfusion, and thus reduced tissue oxygenation, can occur when a patient experiences hemodynamic compromise due to an arrhythmia. When normal sinus rhythm is restored, either spontaneously or as a result of a delivered therapy, the hemodynamic function of the heart will return and tissue perfusion will improve. Accordingly, embodiments described herein utilize the tissue oxygenation measurements for detecting improved tissue perfusion as evidence of a successful arrhythmia therapy.

A hemodynamically stable arrhythmia is a heart rhythm during which cardiac hemodynamic function maintains adequate tissue oxygenation. A rapid cardiac rhythm that is hemodynamically unstable, i.e. results in inadequate tissue oxygenation that leads to tissue hypoxia, is referred to herein as a shockable rhythm in that a cardioversion or defibrillation shock is typically required to restore sinus rhythm and hemodynamic function of the heart. It is recognized that other cardiac rhythm conditions, such as pulseless electrical activity (PEA), electromechanical dissociation (EMD), and asystole can be hemodynamically unstable but such conditions are typically not "shockable rhythms" in that these rhythms typically do not respond to a shock therapy.

FIG. 1 is a schematic drawing of an implantable medical device (IMD) 10 configured for both monitoring the function of and delivering therapy to heart H. In FIG. 1, heart H is shown in a partially cutaway view illustrating right atrium RA, right ventricle RV, left ventricle LV, and coronary sinus CS.

IMD 10 is shown embodied as an ICD that includes a pulse generator for delivering electrical stimulation to heart H for use in cardiac pacing therapies, cardioversion and/or defibrillation. Another example of an implantable medical device in which methods described herein may be practiced would be a subcutaneous cardioverter/defibrillator having electrodes implanted subcutaneously rather than transvenously as described herein.

IMD 10 includes hermetically-sealed housing 12, connector block assembly 14, right atrial (RA) lead 16, right ventricular (RV) lead 18, left ventricular (LV) lead 20, and optical sensor lead 22. IMD 10 further includes circuitry and a power source, which are located within housing 12, for controlling the operation of IMD 10. The circuitry communicates with leads 16, 18, 20, and 22 through electrical connectors within connector block assembly 14. A can electrode is formed on or is a part of the outer surface of housing 12, and may act as an electrode in a unipolar combination with one or more of the electrodes carried by leads 16, 18 and 20.

Leads 16, 18, and 20 extend from connector block assembly 14 to right atrium RA, right ventricle RV, and coronary sinus CS adjacent left ventricle LV, respectively, of heart H. Leads 16, 18, and 20 each carry one or more electrodes for sensing EGM signals attendant to the depolarization and repolarization of heart H, for providing pacing pulses for causing depolarization of cardiac tissue in the vicinity of the distal ends thereof, and for providing cardioversion/defibrillation shocks. When provided, a shock is typically delivered between a combination of electrodes carried on RA and RV leads 16 and 18 and the can electrode.

IMD 10 may include an optical sensor 26 along the housing 12 for emitting light into a tissue volume adjacent IMD 10 and detecting light scattered by the tissue volume for measuring light attenuation by the tissue. The measured light attenuation is used to compute tissue oxygenation measurements as will be described herein.

Alternatively or additionally, an optical sensor 24 may be carried by a lead 22 extending from IMD 10. Lead 22 extends from connector block assembly 14 to optical sensor 24, which is extravascularly-implanted, typically subcutaneously or submuscularly, at a desired tissue site. In other embodiments, sensor 24 may be carried by a lead and placed transvenously or transarterially in the blood stream itself. A lead-based sensor may be positioned to transmit light outward through the wall of a vessel to monitor perfusion in adjacent tissue.

Sensor 24 may alternatively be embodied as a wireless sensor, implanted remotely from IMD 10 or worn externally by the patient. Sensor 24 provided as a wireless sensor includes telemetry circuitry for wireless telemetric communication with IMD 10.

Figure 2:
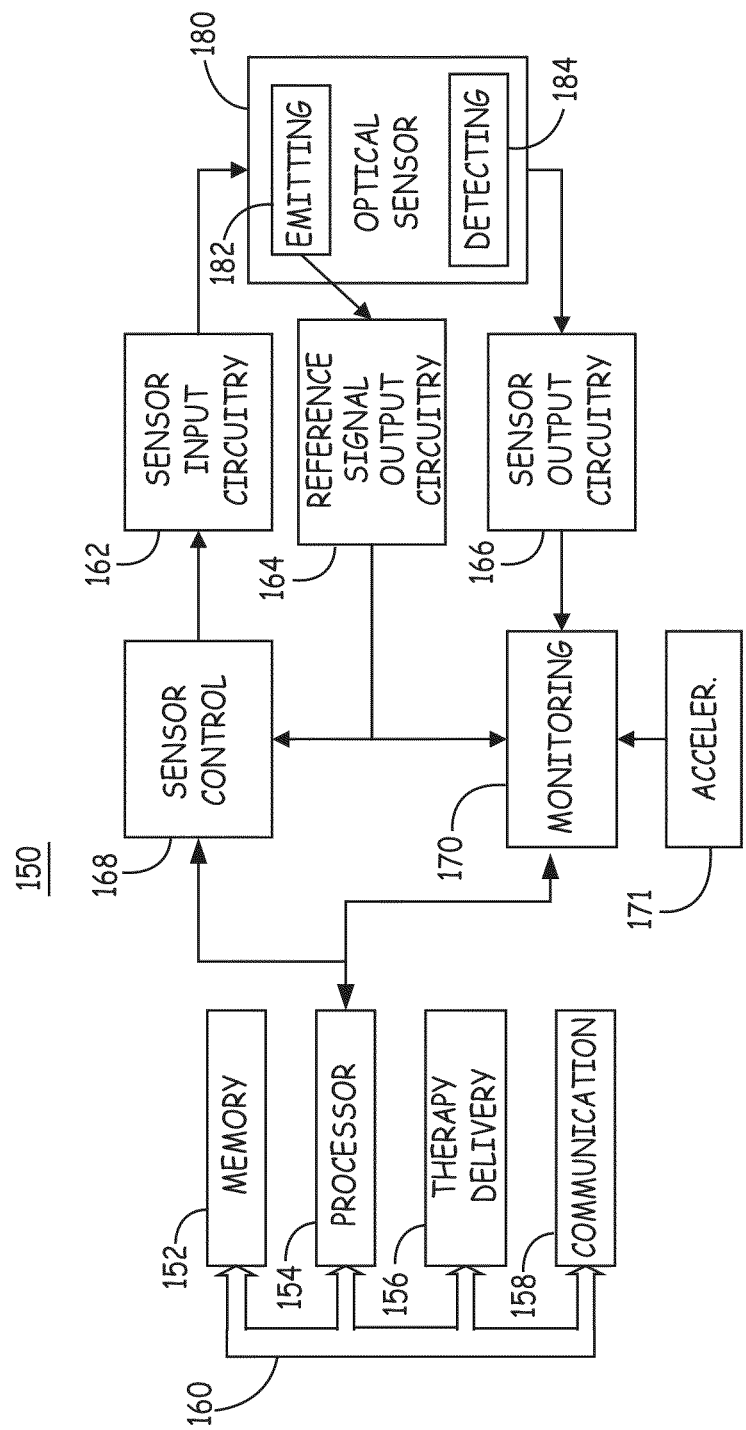
FIG. 2 is a functional block diagram of an IMD associated with an optical sensor for monitoring tissue oxygenation.

FIG. 2 is a functional block diagram of an IMD 150 associated with an optical sensor 180 for monitoring $O_2$Sat and HbT. IMD 150, which may correspond to the ICD shown in FIG. 1, includes (or is coupled to) an optical sensor 180, which may be incorporated in or on a sealed housing of IMD 150 or carried by a lead extending from IMD 150. IMD 150 further includes sensor input circuitry 162, sensor output circuitry 166, and optionally includes reference signal output circuitry 164 when a reference light detector is included in the optical sensor 180 for measuring the intensity of emitted light.

Optical sensor 180 generally includes a light source for emitting light through a blood perfused tissue of the patient and a light detector, also referred to herein as a "photodetector", for generating a signal representative of an intensity of light scattered by the blood perfused tissue to the light detector. In one embodiment, for example, the light passed through the tissue or bloodstream is selected to include four or more wavelengths for use in computing a volume-independent measure of $O_2$Sat, from which an absolute, calibrated $O_2$Sat may be derived. Typically, the intensity of scattered light falling in the red part of the visible light spectrum and the infrared (IR) portion of the light spectrum is measured. The light scattered by the blood perfused tissue and received by the light detector is generally correlated to the oxygenation of the tissue. Changes in tissue perfusion may be caused by changes in hemodynamic function and thus changes in tissue oxygen availability may be used for detecting hemodynamic recovery subsequent to an arrhythmia therapy.

Sensor input circuitry 162 is coupled to a light emitting portion 182 of optical sensor 180. Light emitting portion 182 includes one or more light sources for emitting light that includes two or more different wavelengths. Light sources may emit light at discrete, spaced-apart wavelengths or a single white light source may be used. The measurement of scattered light corresponding to at least four different wavelengths allows calibrated $O_2$Sat and HbT measurements to be obtained as will be described further below. Sensor input circuitry 162 provides input signals to the optical sensor 180. In particular, sensor input circuitry 162 provides the drive signals applied to the light sources included in light emitting portion 182 to cause controlled light emission, e.g. controlled intensity, time duration and frequency.

Sensor input circuitry 162 is controlled by sensor control module 168 which coordinates the beginning time, duration, and frequency of drive signals produced by sensor input circuitry 162. Drive signals may be applied to individual light sources simultaneously to cause "mixed" light emission from all light sources. Control signals may include a period of no light emission for ambient light measurement. In one embodiment, the drive signals are applied sequentially to cause sequential (i.e., non-simultaneous) light emission by individual light sources emitting light at spaced apart wavelengths. In this way, a light detecting portion 184 of sensor 180 will receive scattered light at an individual wavelength at any given time during the operation of sensor 180. It is recognized that referring to an "individual" or "one" wavelength can include a narrow bandwidth of wavelengths approximately centered on, or at least including, the specified individual wavelength emitted by a light source.

The sequential emission of light wavelengths allows multiple, scattered light signals to be sequentially measured for each wavelength. A single $O_2$Sat or HbT measurement will require some minimum interval of time corresponding to the cumulative time durations of each of the separately emitted wavelengths. The time-based sequencing of emitted light may include an interval of no light emission to allow for ambient light measurements and ambient light correction of the measured light signals for the presence of ambient light during light emission by the sensor.

In alternative embodiments, the sensor input circuitry 162 is controlled by sensor control module 168 to deliver drive signals simultaneously to each of the light sources at separate, unique frequencies. Each light source will emit light having a signature frequency fluctuation. The detecting portion 184 will receive scattered light at all of the wavelengths corresponding to the light source wavelengths simultaneously with each wavelength modulated to a signature frequency. A photodetector signal is then demodulated to obtain the individual wavelength signals.

This frequency multiplexing method of controlling the light emitting portion 182 allows simultaneous light emission and detection such that changes in light attenuation by the tissue due to oxygen and hemoglobin changes in the measurement tissue volume can be measured simultaneously for all of the wavelengths rather than at discrete time intervals. This allows for a more instantaneous measurement of $O_2$Sat and HbT as compared to the sequentially-acquired signals for separate wavelengths in the time-multiplexed method of controlling light emission.

The different wavelengths may be modulated at frequencies that are much greater than the frequency of ambient light changes. Demodulation of the detected light signal will reduce or eliminate effects of ambient light artifact since the low frequency components of the detected light signal corresponding to ambient light changes will be substantially removed from the demodulated photodetector output signal.

Sensor output circuitry 166 receives the photodetector signal from light detecting portion 184 and demodulates and digitizes the signal to provide a digital signal to monitoring module 170. Sensor output circuitry 166 may include an analog-to-digital converter and flash memory for digitizing an analog output signal from detecting portion 184, providing the digitized signal to monitoring module 170, storing measurement results for future retrieval, as well as storing calibration coefficients.

Monitoring module 170 uses the optical signal to compute tissue oxygenation measurements using the intensities of the multiple wavelengths measured by detecting portion 184. In some embodiments, a calibrated absolute $O_2$Sat and calibrated HbT are derived from the measurements and provided to a processor 154 (or other control circuitry) for determining the cardiac response to an arrhythmia therapy. In particular, the $O_2$Sat and HbT measurements may be used to determine if the arrhythmia therapy, in particular a shock therapy, is successful or unsuccessful in terminating the arrhythmia based on an improving tissue oxygenation measurement as evidence of restored hemodynamic function.

As described above, IMD 150 is coupled to electrodes for use in sensing intracardiac EGM signals or subcutaneous ECG signals for detecting an arrhythmia. IMD 150 may include other sensors for sensing physiological signals such as blood pressure, patient activity, patient posture, temperature, or the like. Such sensor signals may be used in combination with the monitored tissue oxygenation measurements for determining when a therapy is needed and delivered by therapy delivery module 156 and for determining when an arrhythmia therapy is successful in restoring hemodynamic function. For example, in one embodiment, an accelerometer 171 is included for use in detecting patient motion. Monitoring module 170 receives a signal from accelerometer 171 for use in filtering the optical sensor signal during intervals of time that motion artifact is likely present. As will be further described below, an accelerometer may be used to detect motion caused by delivery of a shock therapy for defining a blanking interval during which tissue oxygenation measurements are not performed.

Therapy delivery module 156 includes electrical pulse generation capabilities for delivering cardiac pacing pulses and cardioversion/defibrillation shocks. Therapy delivery module 156 may additionally include a fluid delivery pump for delivering a pharmaceutical or biological fluid to the patient.

Data acquired by processor 154 relating to $O_2$Sat and HbT may be stored in memory 152 and/or transferred to a medical device programmer, home monitor, computer, or other external or bedside medical device via wireless communication module 158 for review by a clinician. Processor 154 transmits data to and from memory 152, therapy delivery module 156, and communication module 158 via data/address bus 160.

Communication module 158 may be embodied as a wireless telemetry module for communicating with an external device such as a programmer or home monitor. In other embodiments, communication module 158 may be configured for communication via a wireless communication network. Communication module 158 may be used to generate an emergency alarm transmitted to a clinician, centralized database, emergency responder, hospital, or clinic in response to detecting a serious patient condition according some embodiments.

As will be described herein, some embodiments include a reference photodetector in the light emitting portion 182 of sensor 180. Reference signal output circuitry 164 is included for receiving a light detection signal from the reference photodetector and providing a reference output signal to sensor control 168 and/or to monitoring module 170. In one embodiment, the reference signal output circuitry provides an emitted light intensity feedback signal to sensor control 168 in a feedback control loop to maintain emitted light at each wavelength at desired relative intensities. Drive signals applied to a light source in light emitting portion 182 can be automatically adjusted to maintain the emitted light within a desired intensity range for each wavelength measured by the detecting portion 184. In this way, the emitted light spectra is reliably maintained over time promoting the accuracy of $O_2$Sat and HbT measurements computed using stored calibration constants or assuming stable light emission intensity. Accordingly, sensor control 168 may include comparators and other logic circuitry for determining if a reference emitted light intensity signal is within a target range. If not within the desired range, the drive signal is adjusted by sensor control 168, e.g., in an iterative manner, until the target range is reached.

In an alternative embodiment, the reference emitted light intensity signal provided by circuitry 164 is received by monitoring module 170. Monitoring module 170 may use the emitted light intensity and a detected light intensity to compute light attenuation at each desired wavelength. The attenuation at each wavelength is used to compute second derivative attenuation spectra as will be described in greater detail below, which enables derivation of a volume-independent measure of tissue oxygen saturation.

Alternatively, monitoring module 170 uses changes in the emitted light intensity to adjust a computed $O_2Sat$ value. $O_2Sat$ value may be computed assuming a stable emitted light intensity. The actual emitted light intensity may be measured and used to adjust a computed $O_2Sat$ measurement. For example, an initially measured emitted signal intensity and a currently measured emitted signal intensity can be used to adjust or correct an absolute tissue oxygenation measurement computed using only the photodetector signal from detecting portion 184 and calibration constants.

Figure 3:
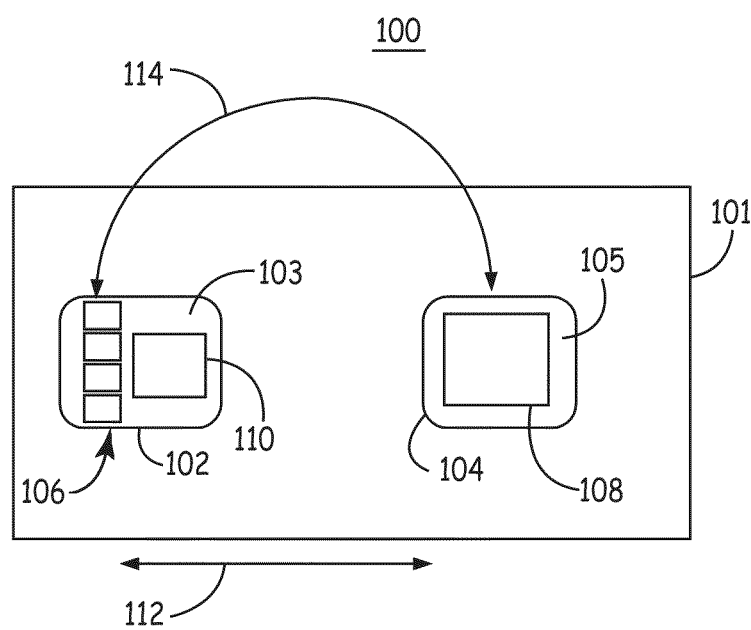
FIG. 3 is a top, schematic view of an optical sensor according to one embodiment.

FIG. 3 is a top, schematic view of an optical sensor according to one embodiment. It is recognized that numerous sensor configurations may be used in methods for monitoring tissue oxygenation for determining shock success as described herein. In general, any optical sensor that acquires measurements of light attenuation in a tissue volume which can then be used to compute a measurement correlated to tissue oxygenation may be used. In some embodiments, tissue oxygenation measurements may include a non-calibrated index of oxygen saturation determined using a two-wavelength optical sensor, typically emitting and detecting red and infrared light, as generally disclosed in U.S. Patent Application No. 2007/0255148 (Bhunia), hereby incorporated herein by reference in its entirety. In other embodiments, tissue oxygenation measurements may include non-calibrated indices of oxygen saturation and blood volume determined using a two-wavelength (typically red and infrared) optical sensor or a three-wavelength (typically red, isosbestic and infrared) optical sensor as generally described in U.S. Patent Publication No. 2008/0208269 (Cinbis, et al), hereby incorporated herein by reference in its entirety.

In the illustrative embodiments described herein, calibrated measures of $O_2Sat$ and HbT are measured using a four wavelength optical sensor. Second derivatives of attenuation spectra can be used to obtain a calibrated, measurement of $O_2Sat$ and a calibrated measurement of HbT. Determination of absolute calibrated measures of $O_2Sat$ and HbT allows tissue oxygenation at a particular time point to be evaluated as well as long-term and short-term changes in tissue oxygenation (e.g. over second, minutes, hours, days or weeks) to be monitored. The use of non-calibrated indices of tissue oxygen saturation and blood volume available from 2- or 3-wavelength optical sensor devices allows short term trends in tissue oxygenation (for example over seconds or minutes) to be monitored. As such either calibrated measures or non-calibrated indices of tissue oxygenation may be used to monitor short-term trends in tissue oxygenation occurring within the first few seconds, e.g. up to approximately minute, after delivery of a shock therapy.

The sensor 100 shown in FIG. 3 includes a light emitting portion 102 and a light detecting portion 104. Light emitting portion 102 includes one or more light sources 106 positioned to emit light through a lens 103 sealed in an opening in hermetically-sealed housing 101. Light sources 106 may be embodied as single white light source or multiple light sources emitting light at separate, spaced-apart wavelengths. Suitable light sources include, without limitation, optoelectronic devices such as light emitting diodes (LEDs), lasers such as vertical cavity surface emitting lasers (VCSELs), luminescent or phosphorescent and incandescent light sources. In one embodiment, light sources 106 are embodied as light emitting diodes (LEDs) emitting light in the visible, e.g., red, and/or infrared light spectrum.

For example, light sources 106 may include four LEDs, as shown, which may emit light at separate wavelengths of 680 nm, 720 nm, 760 nm, and 800 nm, for example. Alternatively, the four LEDs provided as light sources 106 may emit light at 660 nm, 720 nm, 760 nm, and 810 nm. In another embodiment, four LEDs are included emitting light at 720 nm, 760 nm, 810 nm, and 850 nm. In yet another embodiment, four LEDs are included that emit light at 720 nm, 760 nm, 810 nm, and 890 nm. Any combination of LEDs emitting light at any of the wavelengths mentioned herein may be used. Furthermore, it is recognized that the specified wavelengths are approximate and separate light sources may emit a narrow band of light wavelengths which is approximately centered on, or at least includes, the specified wavelength.

In the embodiment shown, the light emitting portion 102 further includes a light detector 110, which may be embodied, for example, as a photodiode. The light entering an adjacent tissue volume from emitting portion 102 may change over time during chronic use of sensor 100 due, for example, to drift in the photonic output of light source(s) 106 and/or changes in the optical properties of the materials encountered by light emitted by light sources 106 before entering an adjacent tissue volume. Reference light detector 110 provides an output signal for measuring or detecting changes in the intensity of the light emitted by emitting portion 102.

The reference light detector 110 output signal can be used in computing or adjusting $O_2Sat$ and HbT measurements as described above in conjunction with FIG. 2. Additionally or alternatively, an output signal from reference light detector 110 can be used as a feed back signal for controlling the drive signals applied to light sources 106 to cause light emission.

In other embodiments, a light detector is not included in the emitting portion. The emitted light intensity is assumed to be stable throughout the usable life of the sensor so as not to introduce significant error in attenuation measurements.

The light detecting portion 104 includes a light detector 108 positioned to receive light through a lens 105 mounted in an opening in housing 101. The light detector 108 may be embodied as a photodiode and receives light scattered by an adjacent tissue volume. Other components suitable for use as a light detector include a photoresistor, phototransistor, photovoltaic cell, photomultiplier tube, bolometer, charge-coupled device (CCD) or an LED reverse-biased to function as a photodiode. The distance 112 between the light sources 106 and the light detector 108 will influence the optical path length 114, shown schematically. Greater spacing (longer distance 112) between the emitting and detecting portions will result in a longer optical path extending deeper in the adjacent tissue volume than relatively shorter distances.

Figure 4:
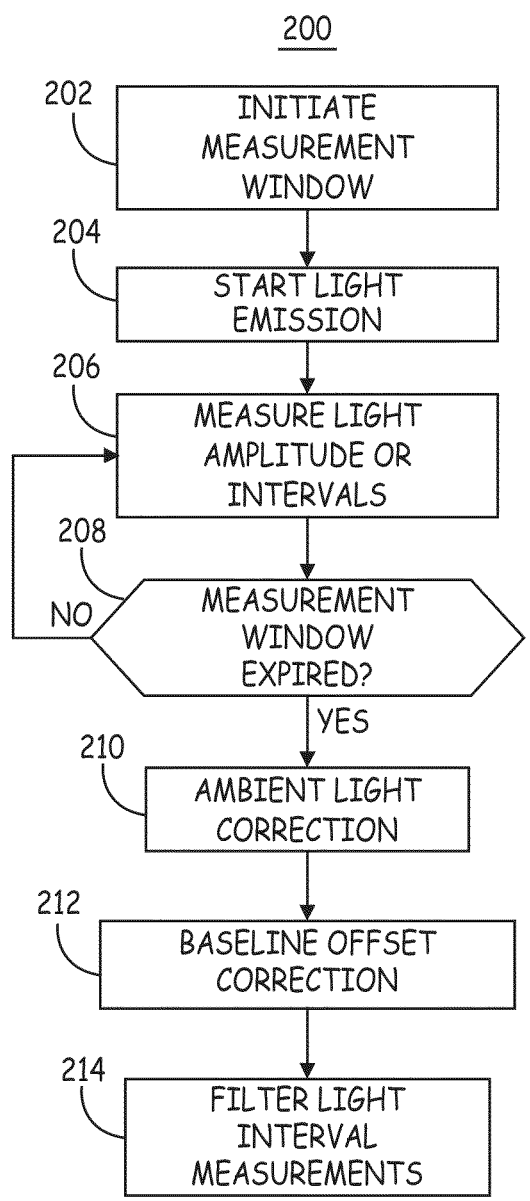
FIG. 4 is a flow chart of a method for operating an optical sensor to obtain photodetector output signals during tissue oxygenation monitoring.

FIG. 4 is a flow chart 200 of a method for operating an optical sensor to obtain photodetector output signals during tissue oxygenation monitoring. Flow chart 200 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing software to accomplish the described functionality in the context of any modern medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 202, a measurement time window is initiated. In other embodiments, tissue perfusion monitoring may be continuous, periodic, or triggered in response to detecting physiological events, such as arrhythmias, monitored by the medical device. According to one embodiment, a measurement window is initiated in response to delivery of a shock therapy. The measurement window may be set to begin before, during or after shock delivery. After initiating the measurement window, light emission is started at block 204. Light emission at selected wavelengths may be controlled in a time multiplexed or frequency multiplexed manner or provided as pulsed or continuous white or mixed light.

At block 206, the electrical output signal produced by the photodetector is measured. The output signal may be analyzed using an amplitude approach or an integration approach. In the integration approach, an integrator is included in the sensor output circuitry for integrating the photodetector signal, for example using a capacitor. The signal may be integrated over fixed time intervals, which may be on the order of approximately 0.10 to 100 ms for example. The magnitude of the integrated signal at the end of the fixed time interval is stored as a sample data point and corresponds to scattered light received by the light detecting portion of the optical sensor during the fixed time interval. Alternatively, the photodetector signal may be integrated until a predetermined integrated signal magnitude is reached and the time interval required to reach the predetermined magnitude is stored as a sample data point.

In other embodiments, the amplitude of the photodetector signal may be monitored directly by sampling the signal amplitude throughout the measurement window. Such sampling may correspond to sequential time intervals of light source activation times during time multiplexed operation. Alternatively the frequency may be selected to be greater than the greatest frequency modulation of a light source in the emitting portion to allow sampling all of frequencies of emitted light in a frequency multiplexed algorithm.

The measurement window may be set to allow time to acquire a desired number of output signal sample points for each of the desired wavelengths. The photodetector signal amplitude or integrated signal amplitude or time interval continues to be sampled during the measurement window until it expires as determined at decision step 208. Depending on whether the measurement window is initiated as a periodic monitoring window or a triggered monitoring window, the duration of the measurement window may vary from a few seconds to a few minutes or longer.

After acquiring the desired number of samples, the drive signals controlling the light emitting portion may be turned off and the sampled data points may be stored and processed for computing $O_2$Sat and HbT as will be described further below. The sampled data points may be filtered or averaged at block 214 to provide smoothing of signal data or removal of artifact.

At blocks 210 and 212 corrections of sampled data may be made to reduce the influence of ambient light and baseline offset. Corrections performed in blocks 210 and 212 may be executed before or after filtering at block 214. Ambient light may be measured directly by measuring the optical signal when the light emitting portion of the optical sensor is not emitting light. The ambient light contribution may then be subtracted from the light signal. Baseline offset (sometimes referred to as the "dark signal" or "dark interval") is caused by current leakage within the optical sensor electronics that occurs in the absence of light. Correction for the baseline offset for a given sensor can be made based on a dark signal or dark interval for that sensor, measured, for example, at the time of device manufacture and qualification testing. If the baseline offset exceeds a desired threshold, offset correction may be included at block 212 to subtract the offset from the incoming signal data. The resulting filtered, corrected sampled signal for each of the wavelengths of interest can be processed, as will be further described herein, for obtaining an $O_2$Sat and HbT for assessing perfusion of the adjacent tissue volume.

Figure 5:
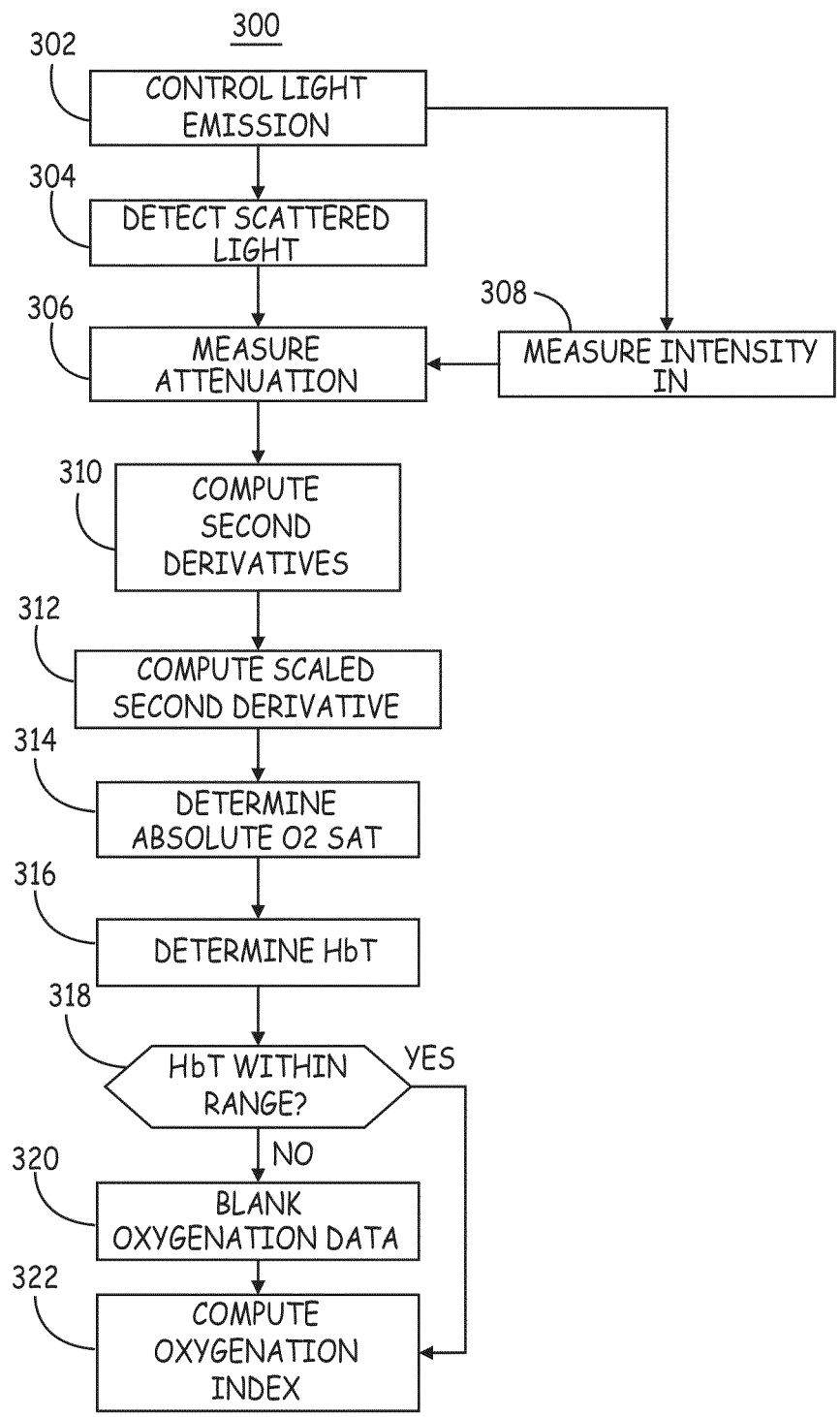
FIG. 5 is a flow chart of a method for operating an optical sensor during tissue oxygenation monitoring.

FIG. 5 is a flow chart of a method 300 for operating an optical sensor during tissue perfusion monitoring. Method 300 generally corresponds to sensor operation after implantation, as will be described in conjunction with FIG. 7. Once the sensor is calibrated and acceptably positioned, it is enabled for monitoring tissue perfusion according to a programmed monitoring algorithm. For example, method 300 generally corresponds to operations performed during a measurement window set on a periodic or triggered basis as described above in conjunction with FIG. 4. The measurement window may also be set as an initial test measurement window during sensor implantation.

At block 302, the light emitting portion of the sensor is controlled to emit light by applying drive signals to the light source(s). As described previously, light sources may be controlled to emit light at different wavelengths in a sequential, time-multiplexed manner or in a simultaneous frequency-multiplexed manner or at multiple simultaneous or mixed wavelengths when filtered in the detecting portion. A reference photodetector included in the light emitting portion provides an output signal for measuring the intensity of light emitted by the sensor at block 308. The output signal is demodulated or otherwise processed to provide an intensity of light emitted for each of the selected wavelengths at which attenuation will be measured.

At block 304, the emitted light scattered by the tissue volume is detected by the photodetector in the light detecting portion. The detecting portion provides an output signal corresponding to the intensity of light received. The output signal is demodulated or otherwise processed to provide an intensity of light received for each of the selected wavelengths.

At block 306, the attenuation spectrum is measured. In one embodiment, the attenuation of four wavelengths in the red to infrared spectrum is measured. The attenuation of the four different wavelengths may be measured using sequential detection of the different wavelengths by the photodetector when a time multiplexed light emission control algorithm is used. Alternatively, measurement of the four different wavelengths may involve demodulation of simultaneously detected light at the four different wavelengths when a frequency multiplexed light emission control algorithm is used. In other embodiments, remitted light from a white light source or simultaneously emitting single wavelength sources may be filtered to obtain the four different wavelength attenuation signals. In still other embodiments, reverse-biased LEDs configured for narrow-band light detection may be used to detect the four separate wavelengths.

The attenuation for a given wavelength ($\lambda$) can be measured as the negative logarithm of the ratio of the emitted light intensity ($i_{in}$) to the remitted light intensity ($i_{out}$):

$$A(\lambda) = -\log(i_{in}/i_{out})_\lambda \quad (1)$$

wherein $i_{in}$ can be measured using a reference photodetector in the light emitting portion of the sensor and $i_{out}$ is measured using the output signal of the light detecting portion for a given wavelength. Remitted light is the light that is scattered by the adjacent tissue volume and received by the light detecting portion of the optical sensor. The term "attenuation measurement" as used herein generally refers to a measure of the attenuation of light due to absorption and scattering by tissue along the optical path of the sensor. The measured attenuation may therefore not be an exact measurement of the actual light absorption by the tissue volume since light reflections and scattering may cause attenuation of the remitted light intensity not attributed to actual light absorption by the tissue.

Alternatively, the emitted intensity $i_{in}$ for each wavelength is measured prior to implantation, e.g., at the time of manufacture, and assumed to be sufficiently stable throughout the usable life of the sensor so as to not cause significant measurement error. In this case, a reference photodetector may be eliminated from the light emitting portion of the sensor and thereby reduce overall size and complexity of the sensor. One method for measuring the emitted intensity prior to implantation uses the light detecting portion to measure the remitted light when the sensor is positioned within a calibrated reflective housing. The construction of the emitting portion is designed to minimize or prevent drift in the emitted light intensity over time. Design considerations include minimizing the distance between the tissue and the photonic surfaces of the light sources.

The attenuation for four wavelengths is determined to allow the second derivative with respect to wavelength of the attenuation spectra at two intermediate wavelengths to be computed. This determination of second derivatives at two intermediate wavelengths allows for computation of a scaled second derivative. By properly selecting the intermediate wavelengths, a scaled second derivative is an oxygen-dependent and volume-independent ratio and therefore provides a measure of $O_2$Sat. At block 310, the attenuation measurement for each intermediate wavelength out of the four detected wavelengths is converted to a second derivative (D"), expressed generally as:

$$D''(\lambda_i) = A(\lambda_{i+1}) - 2A(\lambda_i) + A(\lambda_{i-1}) \quad (2)$$

wherein $A(\lambda_i)$ is the light attenuation, measured according to Equation 1 above, at the wavelength for which the second derivative is being computed, $A(\lambda_{i+1})$ is the attenuation at the next higher wavelength and $A(\lambda_{i-1})$ is the attenuation at the next lower wavelength of the four wavelengths. Equation 2 assumes equal spacings between the four wavelengths. When unequal spacings are used, a different equation for the second derivative with respect to wavelength is required to account for the different wavelength spacings.

The second derivative of a selected intermediate wavelength is scaled by the other computed second derivative at block 312. In one embodiment, the attenuation is measured for wavelengths at 680 nm, 720 nm, 760 nm, and 800 nm. The second derivatives of the attenuation spectra are computed at 720 nm and 760 nm and the second derivative at 720 nm is scaled by the second derivative at 760 nm. The scaled second derivative (SD") of the 720 nm attenuation can be expressed as $$SD'' = D''(720)/D''(760) \quad (3)$$

This SD"(720) is dependent on tissue oxygen saturation and independent of the total hemoglobin and optical path length. The reduced dependence on total hemoglobin and optical path length is expected to reduce the effects of motion artifact on the oxygen measurement.

Once the scaled second derivative is obtained, the stored calibration data is used at block 314 to derive the absolute $O_2$Sat. The second derivative for attenuation at 720 nm wavelength (as well as 760 nm) is dependent on oxygen saturation and total hemoglobin. Thus, at block 316, HbT may be determined knowing the D"(720), or D"(760), with respect to wavelength, the derived absolute $O_2$Sat, and the stored calibration data.

Tissue oxygenation, as defined herein, is a function of both tissue $O_2$Sat and HbT. Depending on the particular tissue oxygenation monitoring application, the derived $O_2$Sat and HbT may each be used separately in a monitoring algorithm or combined to determine a tissue oxygenation index used to monitor a patient's status and/or detect a physiological condition. As will be described herein, post-shock monitoring for hemodynamic recovery of the heart may include monitoring a selected indicator of restored perfusion, e.g. HbT, with other variables such as $O_2$Sat or a tissue perfusion index optionally used to corroborate the finding. At block 322, a tissue oxygenation index may be computed as a function of $O_2$Sat and HbT. For example, a tissue oxygenation index may be a weighted combination of the $O_2$Sat and HbT measurements. In one embodiment, a tissue oxygenation index is computed as:

$$TOI = 0.8 O_2 Sat + 0.2 HbT \quad (4)$$

It is recognized that other weighting factors may be used and the selected weighting factors may even be tailored to an individual patient and a particular monitoring/detection algorithm.

Thus, a tissue oxygenation index computed using absolute measurements of $O_2$Sat and HbT can be available on a continuous or periodic basis in an ambulatory patient. The TOI and/or the individual calibrated values of $O_2$Sat and HbT may be used for tracking a patient's baseline tissue oxygenation, changes in patient status, detecting hemodynamically unstable arrhythmias, and detecting hemodynamic recovery following a shock therapy.

The absolute values of $O_2$Sat, HbT and the TOI computed using the calibrated absolute values of $O_2$Sat and HbT are computed and stored by the ICD. Additionally, differences between each of these oxygenation measures and a baseline or other earlier corresponding measure may be computed and stored as calibrated trended variables. As such, in addition to storing the absolute values, trended values of each of the oxygenation measurements may be stored as changes in the absolute values over time, referred to as $dO_2$ Sat, dHbT or dTOI, which each represent the difference between a current measurement and a previous measurement of the same calibrated measurement.

Alternatively or additionally, non-calibrated values and trends of the oxygenation measurements may be determined and stored. Since sensor calibration can be time consuming and adds to computational burden for computing a calibrated measurement, it may be desirable to compute non-calibrated values and trends of oxygenation measurements without conversion of those measurements to an absolute value. For example, a scaled second derivative of a properly selected wavelength, SD"(λ), is a volume-independent measure of $O_2$Sat and may be computed as an index of $O_2$Sat without conversion to a calibrated measurement. Likewise, D"(λ), which is volume and oxygen dependent, can provide an index of HbT without conversion to a calibrated measurement. Each of these uncalibrated measurements may be used individually as baseline indices of tissue oxygenation or combined in a computation of a TOI, such as a weighted linear combination of the uncalibrated measurements similar to Equation (4) above.

The uncalibrated measurements of $SD''(\lambda)$, $D''(\lambda)$, and a TPI computed using $SD''(\lambda)$ and $D''(\lambda)$ may optionally be determined and stored at device implant for use as baseline measurements and measured during patient monitoring for monitoring patient status and for detecting hemodynamic recovery following a shock therapy. Detection of hemodynamic recovery following a shock therapy may be used to guide a decision to repeat shock delivery or select other therapies or possibly generate notifications according to the hemodynamic and EGM signal status. Trends in each of the uncalibrated measurements over time, referred to as $dSD''(\lambda)$, $dD''(\lambda)$, and dTPI, may also be determined and stored as the difference between a current uncalibrated measurement and a previous corresponding measurement.

In summary, various algorithms for monitoring a patient's tissue oxygenation status and detecting hemodynamic recovery following an arrhythmia therapy may utilize calibrated measurements ($O_2$ Sat and HbT), trends in the calibrated measurements ($dO_2$Sat and dHbt), uncalibrated measurements ($SD''(\lambda)$ and $D''(\lambda)$), and/or trends in the uncalibrated measurements ($dSD''(\lambda)$ and $dD''(\lambda)$) or any combination of the foregoing measurements and trends. Furthermore, indices or trends of indices of tissue oxygenation determined using 2- or 3-wavelength sensors may be used.

The oxygen saturation measurement derived from a scaled second derivative is a volume-independent measurement and is therefore expected to have reduced susceptibility to motion artifact, which could alter the optical pathway and thus alter the measurement volume. However, some embodiments may utilize the measured HbT, which is dependent on the measurement volume, to filter or blank tissue perfusion monitoring during periods in which HbT is out of a normal range, which may be due to motion or activity of the patient.

Accordingly, in one embodiment, the measured HbT is compared to an acceptable range, e.g. between approximately 1% and approximately 25%, at block 318. If HbT is out of the acceptable range, tissue motion may be causing erroneous HbT measurements. At block 320, the tissue perfusion measurement is blanked or otherwise deemed invalid based on the out-of-range HbT measurement. For example, patient activity may result in oscillatory movements that produce a signal that is intermittently in and out of the acceptable range. Shock delivery causes sudden movement of the patient. Intervals in which the HbT measurement is out-of-range may be blanked for determining a tissue oxygenation index. During intervals in which the HbT measurement is in range, the tissue oxygenation index is computed at block 322. When HbT is out of range, the absolute tissue oxygen saturation measurement may also be ignored or still be determined and stored.

Figure 6:
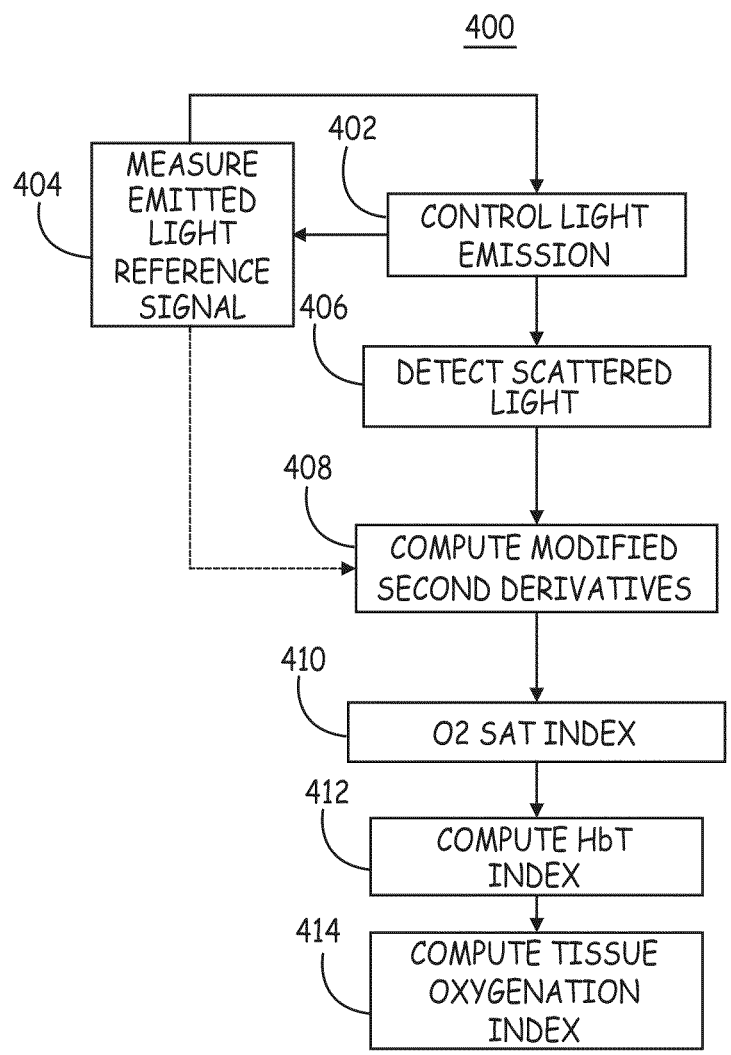
FIG. 6 is a flow chart of an alternative method for using an optical sensor capable of measuring absolute tissue oxygen saturation and total hemoglobin volume fraction for monitoring tissue oxygenation.

FIG. 6 is a flow chart of an alternative method 400 for using an optical sensor capable of measuring absolute tissue oxygen saturation for monitoring tissue oxygenation. At block 402, control signals are applied to drive circuitry to control the emission of light from the light emitting portion of the optical sensor.

In one embodiment, a reference photodetector 110 is included in the light emitting portion to provide a reference signal measuring the emitted light. The intensity of the emitted light may be controlled using a reference feedback signal as indicated by block 404. In other methods, a reference photodetector is used to measure the emitted light intensity for computing the attenuation of each wavelength using Equation 1 above. In method 400, the emitted light intensity is measured using the reference photodetector for controlling light emission such that the emitted intensity ($i_{in}$) at each of the wavelengths used for attenuation measurements is maintained within a specified range.

An emitted light reference signal measured at block 404 using the reference photodetector output signal is provided as feedback to the control module controlling light emission at block 402. Drive signals applied to the light emitting portion may be adjusted in response to the emitted light reference signal to maintain the emitted light intensity within a target range for each wavelength selected for attenuation measurements.

When the emitted light is controlled to be maintained within a specified range, the emitted light intensity ($i_{in}$) in the attenuation Equation (1) above becomes a constant. Manipulation of the second derivative Equation (2) above results in a modified second derivative equation:

$$D''(\lambda_i)_{modified} = C_i - \log(i_{out})_{\lambda_{i+1}} + 2\log(i_{out})_{\lambda_i} - \log(i_{out})_{\lambda_{i-1}} \quad (5)$$

which may be rewritten as:

$$D''(\lambda_i)_{modified} = C_i + \log\{(i_{out})_{\lambda_i}^2/(i_{out})_{\lambda_{i+1}}(i_{out})_{\lambda_{i-1}}\} \quad (6)$$

The term $C_i$ for a given wavelength $\lambda_i$ becomes a calibration constant. Thus, a modified scaled second derivative may be computed using only the detecting portion output signal and the calibration constants $C_i$ determined for each of the measured wavelengths. In the case where there is no reference measurement for emitted light intensities at each wavelength, but the drive signal to the light sources is controllable, the constants Ci are predetermined functions of the drive signal. Note that the above Equation 6 is written for equal wavelength spacing and will include more terms for non-equal wavelength spacing.

The scattered light is detected by the optical sensor at block 406 and used to compute the modified second derivatives at block 408 at two (or more) intermediate wavelengths. The modified second derivatives need only be computed for two intermediate wavelengths being used to compute $O_2$Sat and HbT.

A simplified scaled second derivative may be used as an estimate of tissue oxygen saturation in which the $C_i$ constants are ignored in the above equations. A simplified scaled second derivative may take the form of:

$$SD'' = \frac{-\log(i_{out})_{\lambda_{i+1}} + 2\log(i_{out})_{\lambda_i} - \log(i_{out})_{\lambda_{i-1}}}{-\log(i_{out})_{\lambda_{i+2}} + 2\log(i_{out})_{\lambda_{i+1}} - \log(i_{out})_{\lambda_i}} \quad (7)$$

This simplified scaled second derivative may be useful for measuring an uncalibrated, index of $O_2$Sat at block 410. A corresponding uncalibrated index of HbT may be computed at block 412 using the simplified second derivative computed using Equation 6. The $O_2$Sat and HbT indices may be used individually or combined in a TOI computed as a function of both at block 414.

In addition or alternatively to using the emitted light reference signal as feedback to control light emission, the emitted light reference signal may be used by the monitoring module to adjust the computed modified second derivatives at block 408. Shifts in the intensity of the emitted light may be accounted for by introducing a correction term in the equation used to compute the modified second derivative. Accordingly, an adjusted modified second derivative for a selected intermediate wavelength used to compute absolute oxygen saturation might be computed using:

$$D''(\lambda_i)_{modified} = C_i - \log(i_{out} + CT)_{\lambda,i+1} + 2\log(i_{out} + CT)_{\lambda,i} - \log(i_{out} + CT)_{\lambda,i-1} \quad (8)$$

wherein CT is a correction term determined for each wavelength using the emitted light reference signal and is used to adjust the remitted light intensities $i_{out}$ for each wavelength. The CT may be a positive or negative value.

In the methods described herein for monitoring hemodynamic recovery following an arrhythmia therapy, the modified second derivative computations may be substituted for second derivative computations used in deriving volume-independent indices of $O_2$Sat and indices of HbT.

Figure 7:
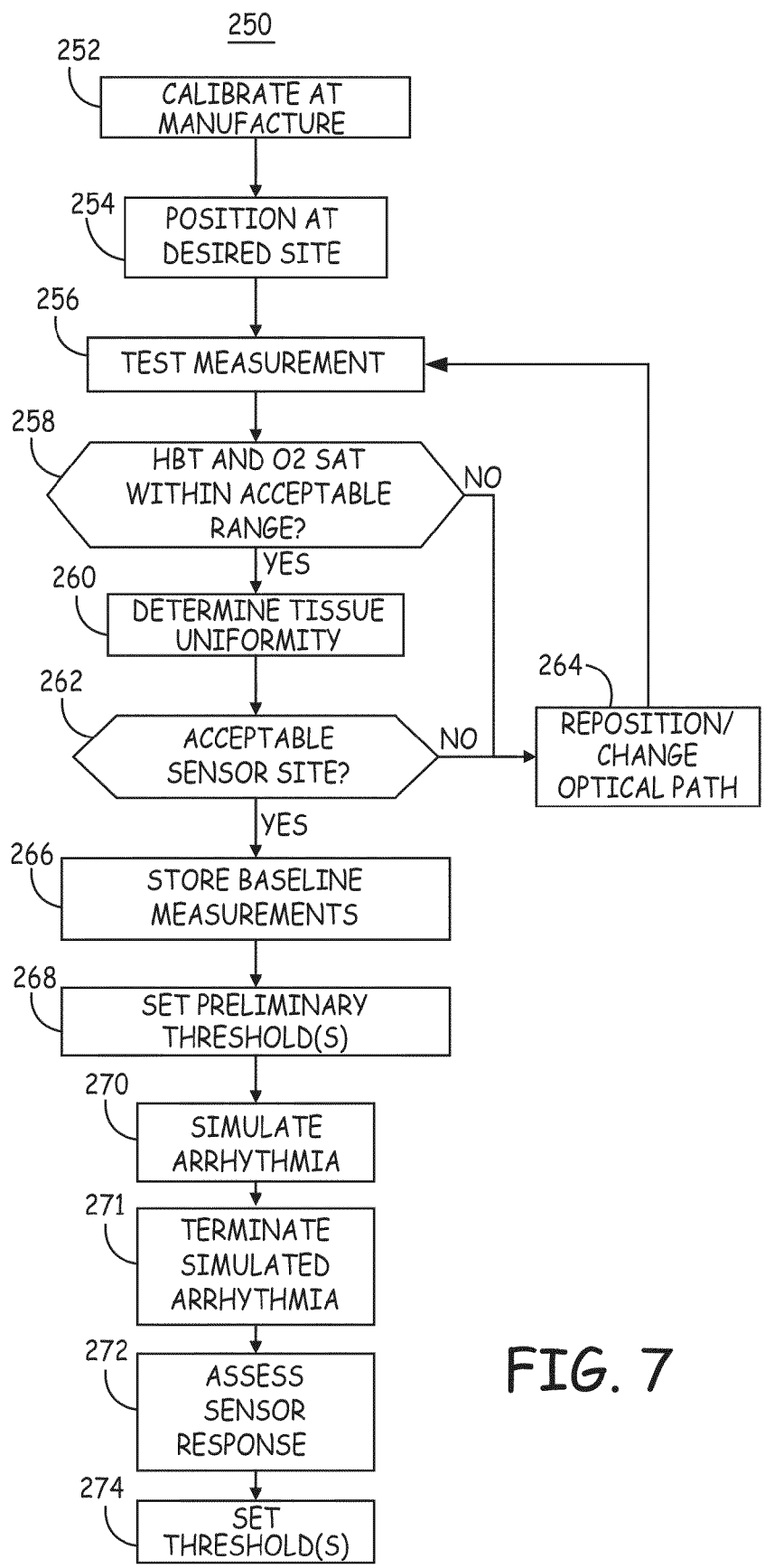
FIG. 7 is a flow chart of a method for using an optical sensor incorporated in an ICD system.

FIG. 7 is a flow chart of a method for using an optical sensor incorporated in an ICD system. At block 252 of method 250, the optical sensor is calibrated using control samples, for example in an in vitro blood circuit, having known oxygen saturation and total hemoglobin concentration. The calibration method may be used to generate a look-up table. A look-up table of values relating measurements computed from the photodetector output signal and the known $O_2$Sat and HbT may be stored in the device memory. The look-up table can then be used to derive absolute $O_2$Sat and Hbt values from an optical sensor measurement, as will be further described below.

Alternatively, calibration methods may include curve-fitting methods to solve for coefficients defining best-fit curves to the calibration data. In one embodiment, the absolute tissue oxygen saturation is defined by:

$$O_2\text{sat} = Ae_i^{B(SD''(\lambda_i))} + C \quad (9)$$

wherein SD" is a scaled second derivative of the attenuation spectra at a selected wavelength ($\lambda_i$). As described above, a scaled second derivative of the attenuation spectra at a selected wavelength is determined by the monitoring module using the photodetector signal. The scaled second derivative is the ratio of the second derivative with respect to wavelength of the attenuation spectra at a selected wavelength $\lambda_i$ to the second derivative of the attenuation spectra at another selected wavelength used for scaling. By properly selecting the wavelength $\lambda_i$ and the other wavelength used for scaling, the scaled second derivative is an oxygen-dependent and volume-independent ratio. The coefficients A, B and C are determined through best-fit analysis of measurements of the scaled second derivative for calibration samples having known oxygen saturation.

The total tissue hemoglobin volume fraction can be defined by the equation:

$$HbT = [M(100 - O_2\text{Sat})^N + L] * [(D''(A)_{\lambda,i}/d\lambda)/SF] \quad (10)$$

wherein M, N, and L are coefficients determined during calibration and $D''(A)_{\lambda,i}/d\lambda$ is the second derivative of the attenuation spectra with respect to wavelength at the selected intermediate wavelength $\lambda_i$. The second derivative of the attenuation spectra with respect to wavelength at a given wavelength is also referred to generally herein as $D''(\lambda)$. $D''(\lambda)$ is measured for samples containing known total hemoglobin volume fraction and known oxygen saturation. The calibration coefficients M, N and L may then be computed for a best-fit of the measured second derivative values and known $O_2$ Sat and HbT. Alternatively, the measured second derivative values and known $O_2$Sat and HbT may be used to generate a look-up table for converting the measured second derivative values to HbT.

SF is a spacing factor which may be used to adjust for an emitting-to-detecting portion spacing that may be different during measurements than that used during calibration. Since the HbT measurement is dependent on both $O_2$Sat and the measurement volume, and measurement volume is dependent on the optical pathway defined at least in part by the spacing between the emitting and detecting portions, the HbT measurement needs to be corrected for changes in emitting-to-detecting portion spacing. For example, the sensor may be calibrated using a nominal emitting-to-detecting portion spacing, however when multiple emitting and/or detecting portions are selectable in a sensor or combination of sensors, the spacing may be different during monitoring than that used during calibration. As such, a spacing factor corresponding to selectable emitting and detecting portions may be stored and used to correct the HbT measurement when a different spacing is used during monitoring than during calibration.

At block 254, the sensor is positioned at a desired implant site (or external site in the case of an external device to be worn by the patient). A test measurement is performed at block 256. The absolute $O_2$Sat and HbT are determined from the sensor output signal using the stored calibration data. The measured values are compared to an acceptable measurement range at block 258. This comparison may be performed manually or automatically using a programmed range stored in the medical device memory. An acceptable measurement range generally corresponds to an expected physiological range for $O_2$Sat and HbT. For example, an acceptable range for tissue $O_2$Sat might be defined to be between approximately 80% and 90%. An acceptable range for HbT might be defined to be between approximately 1% and 25%. These ranges may vary depending on the type of tissue adjacent to the sensor, the heterogeneity of the tissue, the oxygenation state of the patient and other factors. The acceptable measurement range may be defined nominally or tailored to a given patient.

If the tissue oxygen saturation exceeds a predefined expected range, for example greater than approximately 90%, the sensor may be in a position that results in arterial blood strongly contributing to the tissue oxygen saturation measurement. If the monitoring application is concerned with measuring tissue perfusion, e.g. in skeletal muscle, rather than arterial oxygen saturation, the sensor may be repositioned at block 264.

Likewise, if the oxygen saturation is too low, for example less than approximately 80%, the sensor may be in a position that results in venous blood strongly contributing to the oxygen saturation measurement. If the absolute oxygen saturation falls below an expected physiological range for the particular sensing application, the sensor may be repositioned at block 264.

If the total hemoglobin is less than a predetermined range, for example less than approximately 1%, the sensor may be improperly positioned against the tissue (poor tissue contact) or in a position over a non-tissue medium or low or non-perfused tissue. For example, if the sensor is positioned over fat, scar tissue, clear body fluids, or other implanted medical device components, the total tissue hemoglobin concentration may be below a normal physiological range for perfused tissue. A total tissue hemoglobin of greater than an acceptable physiological range, for example greater than approximately 25%, may indicate blood pooling in the measurement volume beneath the sensor or other sensor measurement error. If the HbT test measurement is outside a predefined acceptable range, the sensor may be repositioned at block 264.

Once the $O_2$Sat and HbT measurements are confirmed to be in an acceptable physiological range for the tissue being monitored, at block 258, a tissue uniformity index may be determined at block 260. A tissue uniformity index is determined by utilizing at least two different emitting-to-detecting portion spacings. Accordingly, at least two different combinations of light sources and light detectors at two different spacings must be available, on the same or different optical sensors, positioned adjacent a target tissue volume.

When at least two different spacings are available, the absolute tissue oxygen saturation is measured using the two different spacings and compared. A tissue uniformity index may be computed based on the difference between two or more measurements performed using different emitting-to-detecting portion spacing. Each measurement would involve different measurement volumes defined by different measurement pathways extending through the tissue. For example, a relatively greater emitting-to-detecting portion spacing would result in greater depth of the measurement pathway and measurement volume.

If the difference between two measurements is small, the tissue is relatively uniform through the depth of the larger measurement volume. If the difference between two measurements is large, the tissue is non-uniform heterogeneous. A threshold for detecting uniform, homogeneous tissue versus non-uniform, heterogeneous tissue volumes may be selected according to a particular application. Detection of heterogeneous tissue may warrant repositioning of the sensor. A tissue uniformity index may indicate the most appropriate emitter-to-detector spacing for measuring within a desired tissue volume and therefore guide selection of light sources and light detectors when multiple combinations are available.

In summary, the initial $O_2$Sat, HbT, and tissue uniformity measurements can be used individually or in combination to decide if the sensor position is acceptable at block 262. If not the sensor may be repositioned at block 264. Instead of repositioning the sensor when unacceptable tissue uniformity or HbT or $O_2$Sat measurements are obtained, a different optical path may be selected by selecting a different combination of light source(s) and light detector when available. For example, multiple light sources and light detectors may be available in one or more sensors to allow selection of different optical paths.

If the sensor position is acceptable, the sensor is fixed at the desired site, and baseline $O_2$Sat and HbT measurements may be acquired and stored at block 266 according to the needs of the particular sensing application. Baseline measurements may be acquired for comparison to future measurements, for use in learning algorithms performed during clinical interventions or during naturally occurring arrhythmias for use in setting thresholds applied to tissue oxygenation measurements.

At block 268 preliminary detection thresholds are set for detecting post-shock hemodynamic recovery. A detection threshold may be set as a percentage change or other defined interval from an initial post-shock measurement or other initial measurement taken just prior to or during the shock.

After setting preliminary thresholds at block 268, pulses may be delivered to the heart to simulate a naturally-occurring arrhythmia at block 270. Arrhythmia simulation may include delivering high rate pacing pulses to simulate a fast tachycardia or delivering pulses to induce tachycardia or fibrillation. Current clinical practice often includes inducing a ventricular fibrillation (VF) episode during an ICD implantation procedure to verify an acceptable defibrillation shock threshold. After inducing VF at block 270, a defibrillation shock is delivered at block 271 to terminate the induced VF. In other practice, an arrhythmia may be simulated at block 270 by delivering high rate ventricular pacing to simulate ventricular tachycardia. In this case, the high rate pacing is terminated at block 271 to allow an intrinsic sinus rhythm to be restored.

The optical sensor response to a simulated arrhythmia is assessed at block 272. For example, measurements obtained continuously or at predefined time points before, during and after the defibrillation shock following a simulated arrhythmia may be compared to assess the change in $O_2$Sat, HbT, and/or a tissue oxygenation index computed from the measured $O_2$Sat and HbT. Changes in the oxygenation measurements and comparisons of the measurements to the preliminary thresholds set at block 268 can be used to determine if an appropriate detection of hemodynamic recovery is made following a simulated arrhythmia.

Adjustment of the preliminary threshold(s) may be made based on the sensor response. Adjustments may be made manually or automatically by the device. If an appropriate recovery detection is made, the preliminary thresholds are accepted and set as the detection thresholds at block 274. If not, the thresholds are adjusted appropriately based on the oxygenation measurements following shock delivery. If an appropriate recovery detection is made, but a large difference exists between the threshold(s) and the oxygenation measurements, the threshold may be adjusted to provide greater sensitivity to detecting hemodynamic recovery and discriminating between a successful and unsuccessful shock therapy.

Figure 8:
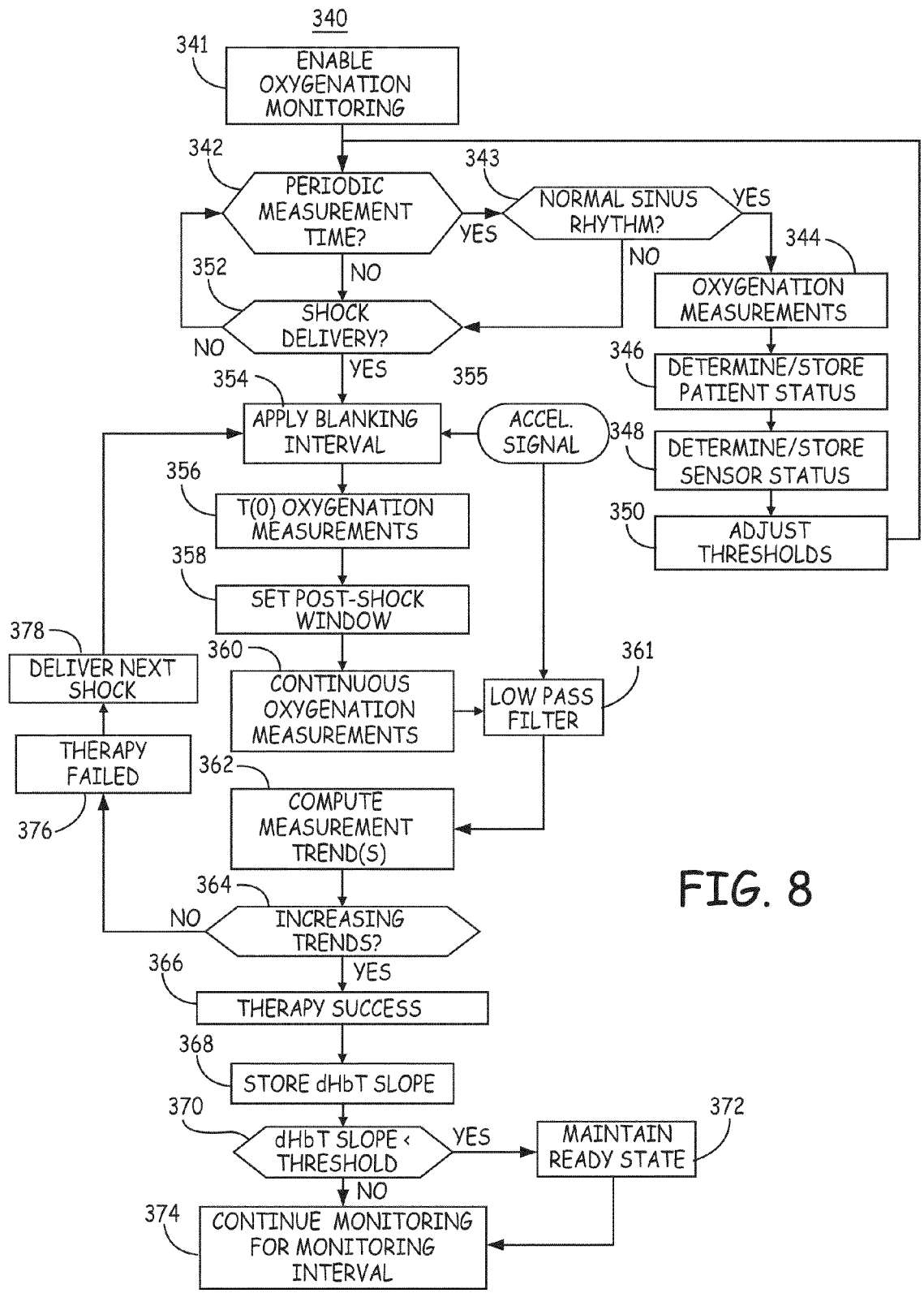
FIG. 8 is a flow chart of a method for monitoring patient status and determining success of an arrhythmia therapy

FIG. 8 is a flow chart of a method 340 for monitoring patient status including monitoring for hemodynamic recovery following an arrhythmia therapy. At block 341, perfusion monitoring is enabled. Tissue oxygenation monitoring may be enabled at the time of device implantation based on acceptable sensor positioning, baseline measurements, and sensor response to a simulated arrhythmia episode.

Tissue oxygenation measurements may be performed on a periodic basis for assessing patient status, sensor function, and resetting baseline measurements or adjusting thresholds applied to tissue oxygenation measurements for detecting hemodynamic recovery or other events. In particular, tissue oxygenation measurements are performed on a triggered basis upon delivery of a shock therapy to the heart for determining shock therapy outcome. While methods described herein relate to monitoring hemodynamic recovery following a shock therapy, assessment of hemodynamic function following other types of arrhythmia therapies may be performed as well using the tissue oxygenation monitoring methods described herein.

At block 342, the device determines if it is time to perform periodic measurements, e.g. based on expiration of a periodic timer. Periodic measurements may be obtained at any desired time interval, for example hourly, daily or weekly. Periodic time measurements may be adjusted automatically or manually if measurements are desired on a more or less frequent basis. For example, if a change greater than a predetermined percentage or predefined range is detected since a previous measurement, the frequency of periodic measurements may be increased to allow closer monitoring of patient status.

If it is time for performing periodic measurements, the ICD confirms the patient is in normal sinus rhythm at block 343. Normal sinus rhythm is typically verified based on regular EGM event intervals (P-P intervals or R-R intervals) occurring at a rate less than a tachycardia detection rate. If normal sinus rhythm is present, the tissue oxygenation measurements are performed at block 344. Performing tissue oxygenation measurements involves computing the uncalibrated $SD''(\lambda)$ and $D''(\lambda)$ values. These values may be stored as indices of $O_2$Sat and HbT or converted to calibrated absolute $O_2$Sat and HbT measurements using stored calibration data when available. A TOI may then be computed using the uncalibrated $SD''(\lambda)$ and $D''(\lambda)$ values and/or the calibrated $O_2$Sat and HbT.

At block 346, the measurements are stored and may be used to determine a patient status. For example, a patient tissue oxygenation status may be indicated as low or normal based on the oxygenation measurements. A low or hypoxic status may warrant more frequent patient monitoring or generating a warning provided to the patient or to a clinician.

At block 348, the oxygenation measurements may be used to determine and store a status of the optical sensor. If either of the $O_2$Sat or HbT measurements is out of the acceptable measurement range, the sensor status may be indicated as unreliable. Tissue oxygenation measurements may be temporarily or permanently disabled based on out of range measurements.

The oxygenation measurements performed at block 344 and determination of sensor status at block 348 may be analogous to the measurements and comparisons performed at the time of device implant (with the exception of a simulated arrhythmia) as discussed in conjunction with FIG. 7. In other words, comparisons to acceptable measurement ranges and a measured tissue uniformity index may be used to select a new combination of light source(s) and light detectors (when available) to change the optical path of the sensor, update stored baseline measurements, and/or adjust the detection thresholds applied to the oxygenation measurements as indicated at block 350.

Whenever a shock therapy is needed, as determined at block 352, tissue oxygenation measurements are triggered for use in determining shock success. A shock therapy may be delivered to treat a detected tachycardia or fibrillation according to a programmed menu of therapies. First, a blanking interval may be applied at block 354 during shock delivery. The blanking interval corresponds to an interval of time in which large motion artifact can occur due to delivery of the high voltage shock pulse. The blanking interval may be defined as a nominal interval or based on clinical or empirical measurements of a time interval beginning at shock delivery until motion artifact in the optical sensor signal has subsided.

In some embodiments, an accelerometer signal may be provided as input as indicated by block 355 in determining the end point of the blanking interval following shock delivery. When patient motion has subsided based on an accelerometer signal, the blanking interval is terminated. A blanking interval is expected to be on the order of approximately 0.5 seconds up to approximately 5 seconds and is generally set as short as possible to allow hemodynamic recovery to be detected as quickly as possible after shock delivery. Stated differently, it is desirable to detect a lack of hemodynamic recovery as quickly as possible after shock delivery in order to repeat shock delivery if the initial shock fails to restore hemodynamic function.

Tissue oxygenation measurements are performed at block 356 upon expiration of the blanking interval and stored as initial T(0) measurements. In alternative embodiments, T(0) measurements may be performed just prior to shock delivery, e.g. during charging of capacitors used to deliver the high energy shock pulse. In still other embodiments, an initial T(0) measurement may be made immediately upon detecting an arrhythmia with additional measurements optionally taken at selected time points leading up to and/or immediately after shock delivery.

Absolute $O_2$Sat and HbT may be measured at block 356. Alternatively, for the purposes of detecting hemodynamic recovery after an arrhythmia therapy, uncalibrated measurements may be computed without conversion to absolute, calibrated values. During a post-shock episode, the use of the uncalibrated values may save processing time allowing a trend in tissue oxygenation measurements to quickly be determined that indicates restored tissue perfusion associated with shock therapy success or ongoing tissue ischemia due to hemodynamic compromise associated with shock therapy failure. As used herein, "success" of a shock therapy refers to restoration of perfusion as indicated by an increasing tissue oxygenation measurement, e.g., an increasing HbT. Blood pressure is one example of a more direct measure that could be used for detecting restored hemodynamic function. HbT is a tissue oxygenation measurement that relates to the perfusion of the tissue and can be considered a surrogate for blood pressure in detecting restored hemodynamic function. "Failure", or "non-success", of a shock therapy as used herein generally refers to failure to measure an increase in a tissue oxygenation measurement corresponding to restored hemodynamic function following shock delivery.

If the perfusion measurements at T(0) are still within the predetermined acceptable measurement range, indicating proper sensor operation, a post-shock detection window is set at block 358. If the T(0) perfusion measurements are outside of an acceptable measurement range, post-shock assessment of tissue oxygenation for shock therapy outcome determination may be disabled. A post-shock detection window may be on the order of approximately 5 to approximately 20 seconds.

During the post-shock detection window, optical sensor measurements are continuously obtained (sampled) at block 360 for computing oxygenation measurements. The oxygenation measurements may be filtered using a low pass filter as indicated at block 361. Low pass filtering may be controlled using feedback from the accelerometer signal 355 to remove high frequency changes in the tissue oxygenation measurements associated with motion artifact due to shock delivery.

A trend in oxygenation measurements is determined at block 362 as the difference between an updated measurement and the T(0) measurement previously determined at block 356 (or any selected reference measurement obtained at a selected time point after arrhythmia detection or immediately after shock delivery). The trends may be trends of calibrated values of $O_2$ Sat ($dO_{2Sat}=O_2$ Sat$_t$-$O_2$ Sat$_{T(o)}$), HbT (dHbT=HbT$_t$-HbT$_{T(0)}$) and/or a TOI (dTOI=TOI$_t$-TOI$_{T(0)}$), computed as a function of both $O_2$ Sat and Hbt. The trends may alternatively be computed for the uncalibrated indices of $O_2$Sat of HbT, i.e. dSD"($\lambda$), dD"($\lambda$) and/or dTOI wherein the TOI is computed as a function of both SD"($\lambda$) and D"($\lambda$).

The trend(s) are then compared to predefined threshold criteria at block 364. A threshold applied to the trends may be defined for each of the oxygenation measurements independently, or a single threshold may be defined for the TOI. For example, if both dHbT and d$O_2$Sat (or the corresponding uncalibrated trends) increase above a predetermined threshold within the post-shock monitoring window, the shock therapy is determined to be successful at block 366. In one embodiment, the dHbT or dD"($\lambda$) is determined at block 362 and compared to a threshold at block 364 to identify an increasing trend. The threshold may be defined, for example, as a fixed difference, as a slope between the T(0) measurement and the current measurement, or a percentage increase from the T(0) measurement.

If dHbT or dD"($\lambda$) is determined to be non-increasing or flat, e.g. based on variation within a predetermined range of the initial T(0) measurement or less than the T(0) measurement, hemodynamic function is determined as not being restored and the shock therapy is detected as a failed therapy at block 376. If dHbT or dD"($\lambda$) is found to increase and remain above a predefined threshold, but d$O_2$Sat or dSD"($\lambda$) does not increase above a predetermined threshold or is decreasing, a confounding physiological condition may exist such as venous blood pooling in the vicinity of the sensor. Accordingly, one or both of the tissue oxygenation measurements relating to HbT and $O_2$Sat may be used to detect restored tissue oxygenation as evidence of hemodynamic recovery following a successful shock therapy. A combination of both HbT and $O_2$Sat measurement trends may be used to discriminate between restored tissue perfusion due to restored cardiac mechanical function and other conditions that may cause disparity between the HbT and $O_2$Sat trends.

If the shock is successful, a time-based slope of dHbT or dD"($\lambda$) or one of the other trended variables may be stored at block 368 as a recovery index. The recovery index is used as an indication of the quality of the arrhythmia recovery. If the recovery is relatively slow or weak, i.e. a low slope of the trended variable, the patient might be more likely to experience a recurring arrhythmia, for example due to myocardial ischemia, or require additional therapeutic support. The time required for hemodynamic recovery following shock delivery may vary between patients, for example depending on their cardiac conduction status. As such, a slope of the trended variable or other recovery index may be evaluated in light of individual patient history or known conduction status.

If the recovery index is less than a predefined threshold, as determined at block 370, the ICD may be maintained in a ready state at block 372 to quickly detect a recurring arrhythmia and/or quickly delivery another shock therapy. In general, a low recovery index may be used to adjust a control parameter used by the ICD in controlling delivery of an arrhythmia therapy following the delivered shock therapy. Such control parameters can include both arrhythmia detection parameters and therapy delivery parameters. For example, arrhythmia detection criteria may be adjusted to allow quicker detection of a recurring arrhythmia. Additionally or alternatively, capacitor charging for shock therapy delivery may be initiated early, e.g. prior to meeting arrhythmia redetection criteria, in response to a poor recovery index or shock therapy control parameters may be adjusted. For example, charging may be initiated upon a predetermined number of fast intervals being detected, prior to confirming an early, recurring arrhythmia detection.

Tissue oxygenation monitoring may continue for a predetermined monitoring interval at block 374 to allow an early or recurring arrhythmia that is hemodynamically unstable to be quickly detected and to assess patient status. The monitoring interval set at block 374 may extend from shock delivery or the expiration of the post-shock window for a relatively longer period of time than the post-shock window. A successful shock therapy but a low level of perfusion based on HbT measurements or low tissue oxygenation based on the oxygenation measurements may warrant clinical attention or additional device-delivered therapies to provide hemodynamic support.

In some embodiments, therapy outcome thresholds used at block 364 to detect a trend of increasing tissue oxygenation measures may be defined based on Principle Component Analysis (PCA) of the tissue oxygenation measurements. PCA involves plotting the $O_2$Sat and HbT measurements (or uncalibrated indices thereof) in a two-dimensional space (or multidimensional space when additional physiological variables are being used in combination with the oxygenation measurements). A vector identifying a first principle component of variation of the plotted measurements is computed. The first principle component of variation of the measurements may be identified for therapy success and/or for therapy failure and used as a template for detecting a shock outcome when the first principle component of monitored oxygenation measurements approach a stored first principal component template for a given outcome.

Additionally or alternatively, a vector identifying a first principle component of variation of the plotted measurements during various confounding situations, such as during motion associated with shock delivery, may be determined for use in artifact removal. In this case, a principle component that is normal (orthogonal) to the first principle component of the plotted measurements in the presence of artifact, e.g. during shock delivery, can be used to remove the effect of the artifact from the measurement variation. This would allow the blanking interval to be eliminated so that oxygenation monitoring can be delivered immediately or even prior to and/or during shock delivery. Principle component analysis methods generally described in U.S. Pat. Appl. No. 61/144,943, incorporated herein by reference in its entirety, may be adapted for use with the tissue oxygenation measurements described herein. For example, an n-dimensional measurement undergoing PCA may include $O_2$Sat and HbT or the uncalibrated values of SD"($\lambda$) and D"($\lambda$) as two of n-dimensions. Alternatively, a TOI computed using a combination of $O_2$Sat and HbT or SD"($\lambda$) and D"($\lambda$) may be included as one of the n-dimensions combined with other physiological variables such a measurement obtained from an EGM signal or other hemodynamic measurements.

If the trended variables do not increase to meet or exceed predefined therapy success threshold criteria, the shock therapy is determined as failed at block 376. The shock may be repeated at block 378, for example using a higher shock energy, according to a programmed schedule of tiered shock therapies. Method 340 then returns to block 354 to apply a blanking interval (if used) and monitor tissue oxygenation during another post-shock monitoring window.

Figure 9:
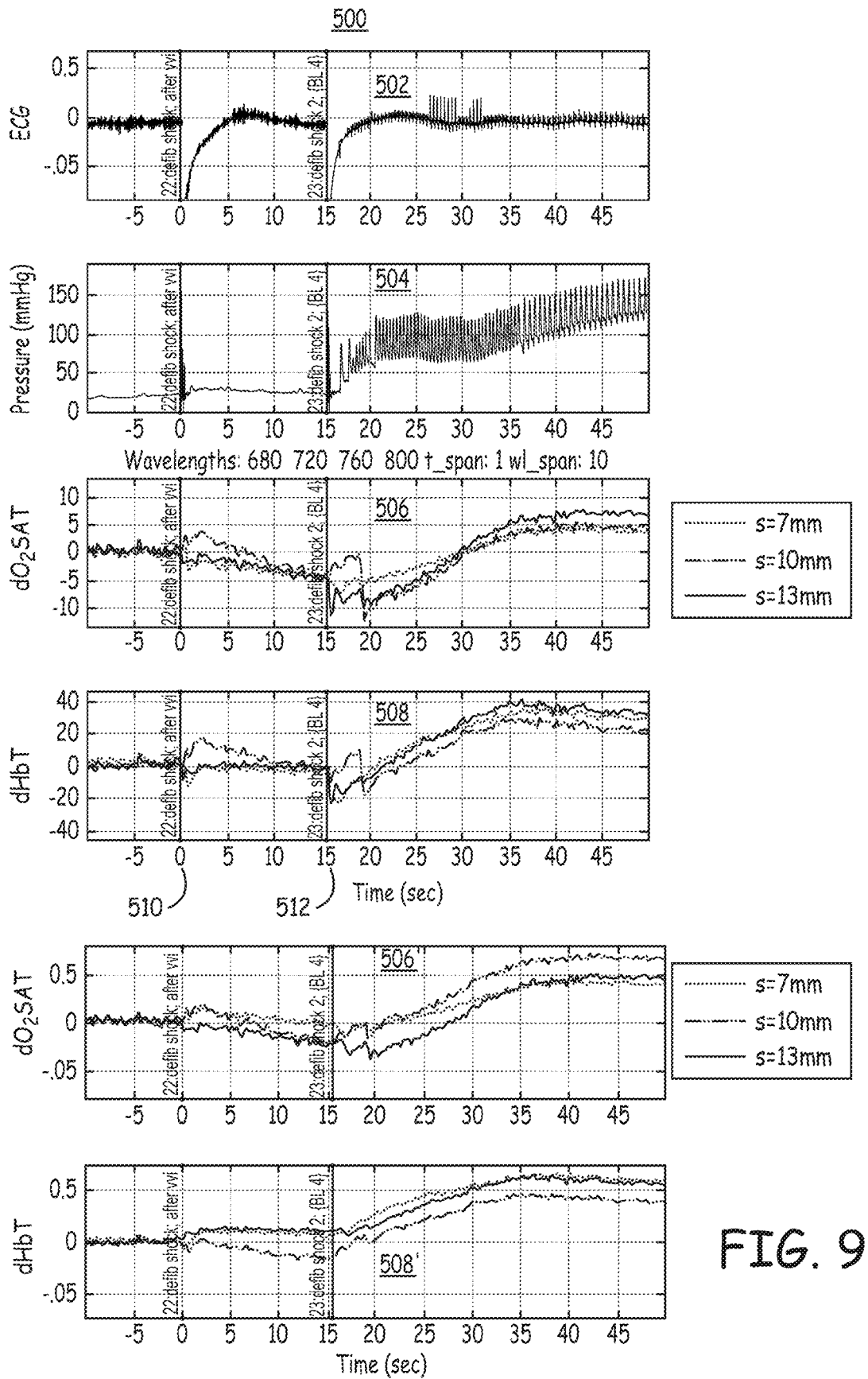
FIG. 9 is a time-based plot of response curves for calibrated trends in oxygen saturation and total hemoglobin volume fraction during induced ventricular fibrillation in a canine subject and delivery of defibrillation shock therapies.

FIG. 9 is a time-based plot 500 of exemplary response curves for calibrated trends in $O_2$Sat and HbT during induced VF and delivery of a defibrillation shock therapy. In ECG 502, blood pressure 504, $dO_2$Sat 506 and dHbT 508 are shown beginning from a time during the induced VF and extending through delivery of a defibrillation shock at time 510 and delivery of a second shock at time 512.

The plotted $dO_2$Sat and dHbT are expressed as percentages of baseline measurements measured just prior to shock delivery. The trended variables $dO_2$Sat and dHbT may be determined as a percentage of a baseline measurement, as shown, or as a difference from a baseline measurement. Attenuation spectra were measured at 680 nm, 720 nm, 760 nm and 800 nm, and the SD"(720) nm and D"(720) were computed from the attenuation spectra. SD"(720) nm and D"(720) were then used to compute calibrated $O_2$Sat and HbT sample points from which the plotted trends were computed. Three different spacings between the light sources and the light detector were used including 7 mm, 10 mm and 13 mm. The results for the three different spacings are plotted and each show similar trends.

The first shock delivered at time 510 failed to restore normal sinus rhythm as observed on the ECG 502 and the flat pressure signal 504. Immediately following shock delivery at time 510, i.e. within the first 1-3 seconds, both $dO_2$Sat 506 and dHbT 508 exhibit an offset due to motion caused by the shock delivery. After the initial offset change, $dO_2$Sat is observed to decline while dHbT remains relatively flat.

Delivery of a second shock at time 512 is followed by restored normal sinus rhythm as observed on the ECG 502 and restoration of normal pulse pressure as observed on the pressure signal 504. After an initial offset change due to motion artifact, $dO_2$Sat 506 and dHbT 508 both exhibit an increasing trend consistent with the return of normal pulse pressure and improved tissue perfusion.

In the bottom two panels, a filtered $dO_2$Sat 506' and filtered dHbT 508' are shown. The filtered $dO_2$Sat 506' is obtained by low pass filtering the $dO_2$Sat 506 signal to remove the offset occurring early after shock delivery. Likewise, the filtered dHbT 508' is obtained after low pass filtering of the dHbT 508 signal. Low pass filtering can remove offset due to shock-induced motion artifact to allow earlier evaluation of measurements and trends following shock delivery. A filtering pass band may be defined using an accelerometer signal for removing higher frequency signal changes caused by motion artifact due to shock delivery.

Response curves similar to those shown in FIG. 9 may be acquired and displayed to a clinician during ICD implantation to allow the clinician to select a sensor implant site, select emitting-to-detecting portion spacings when multiple light sources and/or light detectors are available, storing baseline measurements, and setting detection thresholds. Plots similar to those shown in FIG. 9 may also be generated using stored tissue oxygenation data acquired during detected arrhythmia episodes and shock delivery for later review and analysis by a clinician.

Figure 10:
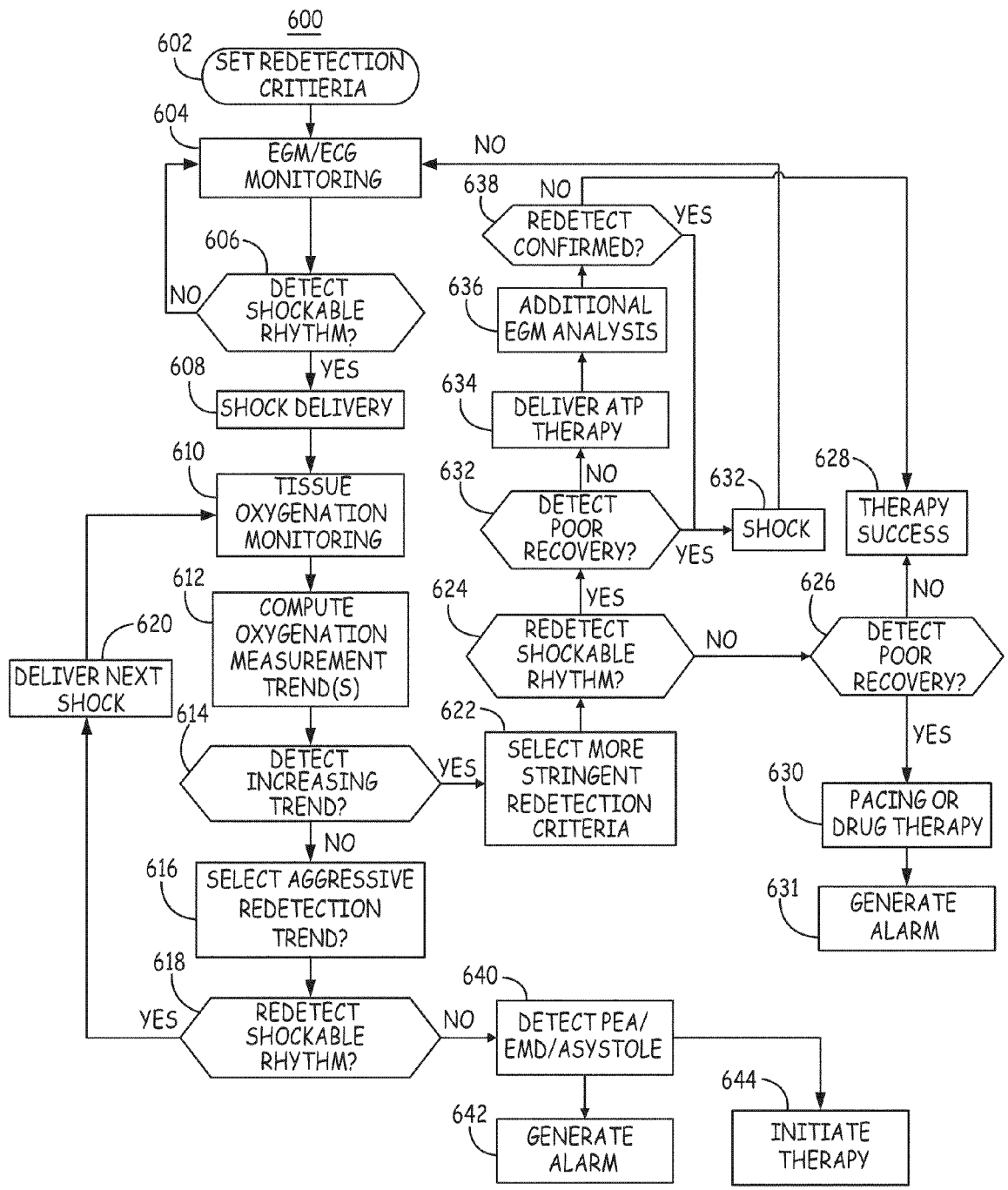
FIG. 10 is a flow chart of a method for monitoring for hemodynamic recovery and guiding therapy delivery decisions following a shock therapy according to an alternative embodiment.

FIG. 10 is a flow chart 600 of a method for monitoring for hemodynamic recovery and guiding therapy delivery decisions following a shock therapy according to an alternative embodiment. At block 602, arrhythmia redetection conditions are set. Redetection conditions may be programmed by a user and stored in memory of the ICD. Conditions for redetection of a shockable rhythm by the ICD may be based on EGM signal analysis alone or on the combination of EGM signals with tissue oxygenation monitoring. It is recognized that depending on the particular medical device being used, subcutaneous ECG signals may be analyzed for detecting a cardiac arrhythmia. As such, when referring to EGM signals herein, it is contemplated that subcutaneous ECG signals could be included or substituted.

When EGM signal analysis is used without tissue oxygenation monitoring for redetecting a shockable rhythm, the redetection criteria that must be met before delivering another shock are typically more aggressive than initial detection criteria. This allows quicker redetection and further attempts at treating the sustained arrhythmia. For example, initial detection criteria may require both rate detection criteria and morphology detection criteria be met. The rate criteria may require eight or ten cardiac cycles falling in a fast tachycardia or fibrillation detection zone. Redetection based only on EGM signal analysis typically requires fewer cardiac cycles, for example, three cardiac cycles within the detection zone, and typically disables morphology detection criteria. Such aggressive redetection criteria allow a potentially fatal arrhythmia to be quickly redetected and treated.

When tissue oxygenation monitoring is enabled and hemodynamic recovery is detected, the redetection criteria based on EGM signal analysis may be less aggressive. Less aggressive redetection when the patient's hemodynamic status is known to be improving or stable allows more time to confirm the heart rhythm based on EGM signals and/or deliver less aggressive therapies such as anti-tachycardia pacing (ATP) therapy.

As such, one set of EGM-based redetection criteria may be established at block 602 for use in the situation when hemodynamic recovery is detected, and a different set of EGM-based redetection criteria may be established for use when hemodynamic recovery is not detected. In some embodiments, a third redetection criteria may be stored for use when tissue oxygenation monitoring is not enabled or oxygenation measurements are deemed unreliable, e.g. due to out-of-range measurements.

At block 604, EGM/ECG signal monitoring is performed. If a shockable rhythm is detected at block 606 according to initial rhythm detection criteria, a shock is delivered at block 608. Post-shock tissue oxygenation monitoring is initiated at block 610. Oxygenation measurement trends are computed at block 612 to determine if an increasing trend is present, as indicated at block 614, indicating restored hemodynamic function. Monitoring tissue oxygenation and detecting an increasing trend in oxygenation measurements can be performed as generally described above in conjunction with FIG. 8.

If an increasing trend is not detected, the redetection criteria stored for use when hemodynamic recovery is not detected are selected at block 616. As described above, these redetection criteria will be relatively more aggressive than initial detection criteria and criteria used when hemodynamic recovery is detected. The more aggressive redetection criteria, for example fewer intervals to detect, allow redetection to occur rapidly. If a shockable rhythm is redetected according to the more aggressive redetection criteria at block 618, another shock therapy is delivered at block 620.

If a shockable rhythm is not redetected at block 618, but hemodynamic recovery has not been detected either, another serious rhythm condition such as pulseless electrical activity, electromechanical dissociation, or asystole may be present as indicated at detection block 640. For example, normal sinus rhythm may be detected based on EGM analysis but the absence of hemodynamic recovery may indicate PEA or EMD. In other cases, neither normal sinus rhythm nor hemodynamic recovery is detected indicating an absence or severe compromise of both electrical and mechanical function.

In any of these situations, the IMD may generate an alarm at block 642. An alarm may include transmitting an emergency message from the implanted device to an external home monitor or programmer. The external device may then transmit an emergency notification to a centralized patient database, networked computer in a clinic or hospital, or other networked communication device, or make a 911 phone call for notifying medical personnel or emergency responders. If the IMD is enabled for wireless communication with a cellular network directly, the IMD may make a 911 phone call. Emergency notification of medical personnel is generally disclosed in U.S. Pat. No. 6,292,698 (Duffin et al.), hereby incorporated herein by reference in its entirety.

In response to detecting neither hemodynamic recovery nor a shockable rhythm, other types of therapies may be initiated at block 644 in an attempt to improve the hemodynamic and/or electrical rhythm condition of the patient. For example, cardiac potentiation therapy (CPT), which may also be referred to as post-extra systolic potentiation (PESP) therapy, may be initiated in an attempt to improve the hemodynamic condition of the patient. Reference is made, for example, to U.S. Pat. No. 6,738,667 (Deno, et al.), incorporated herein by reference in its entirety. Other therapies may include inotropic drug delivery when the IMD includes drug delivery capabilities. Respiratory nerve stimulation may be applied to achieve a resuscitative effect, e.g. as generally described in U.S. Pat. No. 7,277,757 (Casavant, et al.), also incorporated herein by reference in its entirety.

Returning to block 614, if an increasing trend in the oxygenation measurements is detected, the EGM-based redetection criteria stored for use when hemodynamic recovery is detected is selected at block 622. Generally, these redetection criteria will be less aggressive than the redetection criteria selected at block 616. Less aggressive redetection criteria generally requires more time to redetect because more stringent criteria is applied, such as a greater number of intervals to detect. If a shockable rhythm is not redetected at block 624 (using the less aggressive redetection criteria selected at block 622), and hemodynamic recovery is still being detected at block 626 based on improved or still increasing oxygenation measurements, the shock therapy may be determined as successful at block 628. If a shockable rhythm is redetected, sinus is generally present. Sinus rhythm accompanied by the increasing or improved tissue oxygenation generally indicates therapy success.

If a shockable rhythm is not redetected at block 624 in the presence of hemodynamic recovery, the shock may have slowed the cardiac rhythm enough to allow some hemodynamic recovery, but recovery may be poor for a number of reasons. If the hemodynamic recovery is detected but determined to be poor at block 626, for example using a recovery index as described previously, additional therapeutic support may be provided at block 630. Therapies provided at block 630 for improving poor hemodynamic recovery may include anti-tachycardia pacing therapy, CPT, and/or drug delivery. Additional time for analyzing the EGM signal and monitoring the hemodynamic recovery may be taken until hemodynamic recovery and the cardiac rhythm are determined to be normal. An alarm may be optionally generated at block 631 when poor hemodynamic recovery is detected to alert the patient and/or a clinician that the patient's hemodynamic status is compromised.

If a shockable rhythm is redetected at block 624, and the hemodynamic recovery is determined to be good (negative result at block 625), a shock therapy may be delayed by first delivering less aggressive ATP therapy at block 630. Additional EGM signal analysis may then be performed at block 632 including, for example, morphology analysis and checking for oversensing of T-wave or other signal artifact may be performed. For example, different or additional EGM sensing electrodes may be selected to check for oversensing. EGM morphology analysis typically invoked for initial detection and disabled for redetection may be performed to verify the redetection.

If the redetected rhythm is confirmed through additional EGM analysis at block 638, the ICD may deliver a shock at block 632 then return to block 604 for post-shock monitoring. If the redetected shockable rhythm is not confirmed, the therapy is successful as indicated at block 628.

In response to redetecting the shockable rhythm at block 624, capacitor charging may be initiated and a pending shock may eventually be delivered depending on the outcome of the additional therapies delivered at block 634 and/or additional EGM analysis at block 638. For example, if the hemodynamic recovery remains poor and further EGM signal analysis confirms the redetection of the shockable rhythm, a shock may be delivered at block 632. If hemodynamic recovery continues to improve or if the redetection is not confirmed, due to oversensing or other causes, the pending shock may be cancelled.

In other embodiments, capacitor charging may also be delayed when the shockable rhythm is redetected at block 624 and hemodynamic recovery has been detected. Capacitor charging may only be initiated after further hemodynamic monitoring and EGM analysis indicates a need for additional shock therapy.

Thus, a medical device and methods for use have been presented in the foregoing description with reference to specific embodiments. It is appreciated that various modifications to the referenced embodiments may be made without departing from the scope of the disclosure as set forth in the following claims.

I claim:
1. A method of delivering therapy in a medical device, comprising:
   emitting light from an emitting portion of a sensor at a predetermined emitted light intensity to an adjacent volume of tissue at a plurality of wavelengths;
   detecting the emitted light scattered by the volume of tissue to generate corresponding detected light intensity output signals;
   detecting, in the emitting portion of the sensor, a change corresponding to a shift in the emitted light intensity from the predetermined intensity before the emitted light enters the adjacent tissue volume;
   adjusting the detected light intensity output signals in response to the detected change;
   determining a tissue oxygenation index in response to only the adjusted detected light intensity output signals; and
   controlling delivery of a therapy in response to the determined tissue oxygenation index.

2. The method of claim 1, further comprising:
   generating an emitted light reference signal from a reference light detector in the emitting portion configured to detect the emitted light before it enters the adjacent tissue volume; and
   adjusting drive signals associated with the light emission in response to the generated emitted light reference signal.

3. The method of claim 1, wherein the wavelengths of the plurality of wavelengths are equally spaced.

4. The method of claim 1, wherein determining a tissue oxygenation index comprises:
   determining an attenuation measurement for each wavelength of the plurality of wavelengths in response to the detected light intensity output signals;
   determining a second derivative of the attenuation measurement for a first wavelength and a second wavelength of the plurality of wavelengths in response to only the adjusted detected light intensity output signals; and
   determining the tissue oxygenation index in response to the determined second derivative.

5. The method of claim 4, wherein determining a tissue oxygenation index further comprises:
   determining a scaled second derivative of the attenuation measurement of the first wavelength using the determined second derivative of the attenuation of the second wavelength of the predetermined wavelengths; and
   determining the tissue oxygenation index in response to the determined scaled second derivative.

6. The method of claim 5, further comprising determining at least one of an oxygen saturation index and a hemoglobin volume fraction in response to one of the second derivative and the scaled second derivative, wherein the tissue oxygenation index is determined in response to at least one of the oxygen saturation index and the hemoglobin volume fraction.

7. The method of claim 1, wherein adjusting the detected light intensity output signals comprises:
   generating an emitted light reference signal from a reference light detector in the emitting portion configured to detect the emitted light before it enters the adjacent tissue volume;
   determining a correction term in response to the generated reference signal; and
   adjusting the detected light intensity output signals in response to the correction term.

8. The method of claim 1, wherein detecting, in the emitting portion of the sensor, a change corresponding to a shift in the emitted light intensity comprises controlling a drive signal applied to a light source;
   wherein adjusting the detected light intensity output signal comprises adjusting a calibration constant in response to a change in the drive signal.

9. A medical device having a sensor for controlling delivery of therapy by the device, comprising:
- an emitting portion configured to emit light at a predetermined emitted light intensity to an adjacent volume of tissue at a plurality of wavelengths;
- a detecting portion configured to detect the emitted light scattered by the volume of tissue to generate corresponding detected light intensity output signals;
- a control module configured to:
  - detect, in the emitting portion of the sensor, a change corresponding to a shift in the emitted light intensity from the predetermined intensity before the emitted light enters the adjacent tissue volume;
  - adjust the detected light intensity output signals in response to the detected change, and
  - determine a tissue oxygenation index in response to only the adjusted detected light intensity output signals; and
- a therapy delivery module configured to control delivery of a therapy in response to the determined tissue oxygenation index.

10. The device of claim 9, further comprising a reference light detector in the emitting portion for detecting the emitted light before it enters the adjacent tissue volume and generating an emitted light reference signal, wherein the control module adjusts drive signals associated with the light emission in response to the generated emitted light reference signal.

11. The device of claim 9, wherein the wavelengths of the plurality of wavelengths are equally spaced.

12. The device of claim 9, wherein the control module is configured to determine an attenuation measurement for each wavelength of the plurality of wavelengths in response to the detected light intensity output signals, determine a second derivative of the attenuation measurement for a first wavelength and a second wavelength of the plurality of wavelengths in response to only the detected light intensity output signals, and determine the tissue oxygenation index in response to the determined second derivative.

13. The device of claim 12, wherein the control module is configured to determine a scaled second derivative of the attenuation measurement of the first wavelength using the determined second derivative of the attenuation of a second wavelength, and determine the first tissue oxygenation index in response to the determined scaled second derivative.

14. The device of claim 13, wherein the control module is configured to determine at least one of an oxygen saturation index and a hemoglobin volume fraction in response to one of the second derivative and the scaled second derivative, and determine the tissue oxygenation index in response to at least one of the oxygen saturation index and the hemoglobin volume fraction.

15. The device of claim 9, further comprising a reference detector for detecting the emitted light before it enters the adjacent tissue volume to generate an emitted light reference signal, wherein the control module is configured to determine a correction term in response to the generated reference signal and adjust the detected light intensity output signals in response to the correction term.

16. A non-transitory computer readable medium having computer executable instructions for performing a method comprising:
- emitting light from an emitting portion of a sensor at a predetermined emitted light intensity to an adjacent volume of tissue at a plurality of wavelengths;
- detecting the emitted light scattered by the volume of tissue to generate corresponding detected light intensity output signals;
- detecting, in the emitting portion of the sensor, a change corresponding to a shift in the emitted light intensity from the predetermined intensity before the emitted light enters the adjacent tissue volume;
- adjusting the detected light intensity output signals in response to the detected change;
- determining a tissue oxygenation index in response to only the adjusted detected light intensity output signals; and
- controlling delivery of a therapy in response to the determined tissue oxygenation index.

17. The computer readable medium of claim 16, the method further comprising:
- generating an emitted light reference signal from a reference light detector in the emitting portion configured to detect the emitted light before it enters the adjacent tissue volume; and
- adjusting drive signals associated with the light emission in response to the generated emitted light reference signal.

18. The computer readable medium of claim 16, wherein the wavelengths of the plurality of wavelengths are equally spaced.

19. The computer readable medium of claim 16, wherein determining a tissue oxygenation index comprises:
- determining an attenuation measurement for each wavelength of the plurality of wavelengths in response to the detected light intensity output signal;
- determining a second derivative of the attenuation measurement for a first wavelength and a second wavelength of the plurality of wavelengths in response to only the detected light intensity output signals; and
- determining the tissue oxygenation index in response to the determined second derivative.

20. The computer readable medium of claim 19, wherein determining a tissue oxygenation index comprises:
- determining a scaled second derivative of the attenuation measurement of the first wavelength using the determined second derivative of the attenuation of the second wavelength of the predetermined wavelengths; and
- determining the tissue oxygenation index in response to the determined scaled second derivative.

21. The computer readable medium of claim 20, the method further comprising determining at least one of an oxygen saturation index and a hemoglobin volume fraction in response to one of the second derivative and the scaled second derivative, wherein the tissue oxygenation index is determined in response to at least one of the oxygen saturation index and the hemoglobin volume fraction.

22. The computer readable medium of claim 16, wherein adjusting the detected light intensity output signal comprises:
- generating an emitted light reference signal from a reference light detector in the emitting portion configured to detect the emitted light before it enters the adjacent tissue volume;
- determining a correction term in response to the generated reference signal; and
- adjusting the detected light intensity output signals in response to the correction term.

* * * * *